United States Patent
Chavez et al.

(10) Patent No.: US 11,286,470 B2
(45) Date of Patent: *Mar. 29, 2022

(54) MUTANT CAS9 PROTEINS

(71) Applicant: President and Fellows of Harvard College, Cambridge, MA (US)

(72) Inventors: Alejandro Chavez, New York, NY (US); Frank J. Poelwijk, Dallas, TX (US); George M. Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/852,592

(22) Filed: Apr. 20, 2020

(65) Prior Publication Data

US 2020/0283747 A1    Sep. 10, 2020

Related U.S. Application Data

(60) Continuation of application No. 16/440,241, filed on Jun. 13, 2019, now Pat. No. 10,683,490, which is a continuation of application No. 16/157,481, filed on Oct. 11, 2018, now Pat. No. 10,435,679, which is a division of application No. 15/037,696, filed as application No. PCT/US2014/066375 on Nov. 19, 2014, now Pat. No. 10,100,291.

(60) Provisional application No. 61/906,374, filed on Nov. 19, 2013.

(51) Int. Cl.
| | | |
|---|---|---|
| *C12N 9/22* | (2006.01) | |
| *C07H 21/04* | (2006.01) | |
| *C12Q 1/6897* | (2018.01) | |
| *G01N 33/573* | (2006.01) | |

(52) U.S. Cl.
CPC .............. *C12N 9/22* (2013.01); *C07H 21/04* (2013.01); *C12Q 1/6897* (2013.01); *C12Y 301/00* (2013.01); *G01N 33/573* (2013.01); *G01N 2333/922* (2013.01)

(58) Field of Classification Search
CPC ......... C12Y 301/00; C12N 9/22; C07H 21/04
USPC ....................................................... 435/188
See application file for complete search history.

(56) References Cited

U.S. PATENT DOCUMENTS

| | | |
|---|---|---|
| 8,697,359 B1 | 4/2014 | Zhang |
| 9,074,199 B1 | 7/2015 | Chavez et al. |
| 10,100,291 B2 * | 10/2018 | Chavez ................... C12N 9/22 |
| 2010/0076057 A1 | 3/2010 | Sontheimer et al. |
| 2011/0189776 A1 | 8/2011 | Terns et al. |
| 2011/0223638 A1 | 9/2011 | Wiedenheft et al. |
| 2011/0286980 A1 | 11/2011 | Brenner |
| 2013/0130248 A1 | 5/2013 | Haurwitz et al. |
| 2013/0253040 A1 | 9/2013 | Miller et al. |
| 2014/0242700 A1 | 8/2014 | Zhang et al. |
| 2014/0273226 A1 | 9/2014 | Wu |

FOREIGN PATENT DOCUMENTS

| | | |
|---|---|---|
| JP | 2005529837 A | 10/2005 |
| WO | 2008/108989 A2 | 9/2008 |
| WO | 2010/054108 A2 | 5/2010 |
| WO | 2011/143124 A2 | 11/2011 |
| WO | 2012/164565 A1 | 12/2012 |
| WO | 2013/098244 A1 | 7/2013 |
| WO | 2013/126794 A1 | 8/2013 |
| WO | 2013/141680 A1 | 9/2013 |
| WO | 2013/142578 A1 | 9/2013 |
| WO | 2013/169802 A1 | 11/2013 |
| WO | 2013/176772 A1 | 11/2013 |
| WO | 2014/022702 A2 | 2/2014 |
| WO | 2014/150624 A1 | 9/2014 |

OTHER PUBLICATIONS

Al-Attar et al., Clustered Regularly Interspaced Short Palindromic Repeats (CRISPRs): The Hallmark of an Ingenious Antiviral Defense Mechanism in Prokaryotes, Bioi Chern. (20 11) vol. 392, Issue 4, pp. 277-289.
Carroll, "A CRISPR Approach to Gene Targeting" 20(9) Molecular Therapy 1658-1660 (Sep. 2012).
Gasiunas, G et al., Cas9-crRNA Ribonucleoprotein Complex Mediates Specific DNA Cleavage For Adaptive Immunity In Bacteria. PNAS. Sep. 4, 2012. vol. 109, No. 39; pp. E2579-E2586; p. E2583, first col. first paragraph. DOI: 10.1073/pnas.1208507109.
Hale et al., Essential Features and Rational Design of CRISPR RNAs That Function With the Cas RAMP Module Complex to Cleave RNAs, Molecular Cell, (20 12) vol. 45, Issue 3, 292-302.
Hatoum-Aslan, et al. 'Mature clustered, regularly interspaced, short palindromic repeats RNA 5, 9, 14 (crRNA) length is measured by a ruler mechanism anchored at the precursor processing site.' Proceedings of the National Academy of Sciences. vol. 108, No. 52, pp. 21218-21222. Dec. 2011. Entire document.
Jinek , et al. 'RNA-programmed genome editing in human cells.' eLite 2013;2:e00471 . [retrieved 1-3, 6, 7, 10-12 on Jun. 3, 2014). Retrieved from the Internet. <URL: http://elife .elifesciences.org/content/2/e00471 >. Entire document.
Jinek, M et al. A Programmable Dual-RNA-Guided DNA Endonuclease In Adaptive Bacterial Immunity. Science. Jun. 28, 2012. vol. 337; pp. 816-821; DOI: 10.1126/science.1225829.
Makarova et al., "Evolution and classification of the CRISPR-Cas systems" 9(6) Nature Reviews Microbiology 467-477 (1-23) (Jun. 2011).
Rho, Mina et al. 'Diverse CRISPRs Evolving in Human Microbiomes.' PLoS Genetics. vol. 8, No. 6. 1-14 pp. 1-12. Jun. 2012. Entire document.

(Continued)

*Primary Examiner* — Tekchand Saidha
(74) *Attorney, Agent, or Firm* — Banner & Witcoff, Ltd.

(57) ABSTRACT

Methods of making mutant Cas9 proteins are described.

11 Claims, 14 Drawing Sheets
(12 of 14 Drawing Sheet(s) Filed in Color)
Specification includes a Sequence Listing.

(56) References Cited

OTHER PUBLICATIONS

Sontheimer Erik, Project 7: Establishing RNA-Directed DNA Targeting in Eukaryotic Cells; Project dates: Nov. 16, 2011 to Dec. 31, 2012 (Feb. 4, 2012).
Wiedenheft et al., "RNA -guided genetic silencing systems in bacteria and archaea" 482 Nature 331-338 (Feb. 16, 2012).
Van Leeuwen et al.. Linker length and composition influence the flexibility of Oct. 1 DNA binding. EMBO J Apr. 15, 1997, vol. 2043-2053 Especially abstract, p. 2043 col. 2 para 2, p. 2044, fig. 1B.
Chylinski et al.. The tracrRNA and Cas9 families of type II CRJSPR-Cas immunity systems. RNA Bioi May 2013 vol. 10, No. 5, pp. 726-737. Especially p. 727 col. 1, para. 1, p. 727 col. 2, para 2, Suppl. Fig. S1.
Mali et al. CAS9 transcriptional activators for target specificity screening and paired nickases for cooperative genome engineering. Nature Biotechnology ePub Aug. 1, 2013 vol. 31 No. 9 pp. 833-838. Especially p. 5 para 4, Suppl Fig S15.
Zhou et al. Alteration of substrate specificities of thermophilic alpha/beta hydrolases through domain swapping and domain interface optimization. Acta Biochim Biophys Sin Dec. 2012 vol. 44, No. 12 pp. 965-973. Especially abstract.
Esvelt et al. Orthogonal Cas9 proteins for RNA-guided gene regulation and editing. Nature Methods Epub Sep. 29, 2013 vol. 10 No. 11 pp. 1116-1121. Especially p. 1 col. 2 para 4.
International Search Report issued from corresponding PCT/US2014/066375, dated Apr. 17, 2015.
Radziwill, Gerald et al., "Mutational Analysis of the Hepatitis B Virus P Gene Product: Domain Structure and RNase H Activity". Journal of Virology, Feb. 1990, vol. 64 No. 2, pp. 613-620.
Wilson, Gavin W. et al., "Phage T4 mobE promotes trans homing of the defunct homing endonuclease I-Tevlll". Nucleic Acids Research, Sep. 2009, vol. 37, No. 21, pp. 7110-7123.
Jensen, Sanne et al., "Analysis of Functional Domain Organization in DNA Topoisomerase II from Humans and *Saccharomyces cerevisiae*". Molecular and Celullar Biology, Jul. 1996, pp. 3866-3877, vol. 16, No. 7.
Woo-Cho, Seung et al., "Targeted genome engineering in human cells with the Cas9 RNA-guided endonuclease". Nature Biotechnology., Jan. 2013, pp. 230-232, vol. 31, No. 3.
Office Action dated Oct. 16, 2018 for JP 2016-532542.
European Search Report dated Mar. 30, 2020.
Grizot S. et al., "Generation of redesigned homing endonucleases comprising DNA-binding domains derived from two different scaffolds," Nucleic Acids Research, vol. 38, No. 6, pp. 2006-2018 (Apr. 1, 2010). Particularly p. 2007, left col. para. 2; p. 2017, right col. para. 2; and figure 1.
Makarova et al., "Unification of Cas protein families and a simple scenario for the origin and evolution of CRISPR-Cas systems," Biology Direct, vol. 6, No. 1, pp. 1-27 (Jan. 1, 2011). Particularly p. 11, right col. para. 2; p. 12, right col. para 1; and figure 5.
Karvelis et al., "crRNA and tracrRNA guide Cas9-mediated DNA interference in *Streptococcus thermophilus*," RNA Biology, vol. 10, No. 5, pp. 841-851 (Mar. 27, 2013). Particularly the abstract and figure 3.
"Neisseria meningitidis WUE 2594 conserved hypothetical protein," EMBL (Jan. 17, 2011) together with Schoen et al., "Whole-Genome Sequence of the Transformable Neisseria meningitidis Serogroup A Strain WUE2594," Journal of Bacteriology, vol. 193, No. 8, pp. 2064-2065 (Feb. 4, 2011).
Hou et al., "Efficient genome engineering in human pluripotent stem cells using Cas9 from Neisseria meningitidis," Proceedings of the National Academy of Sciences, vol. 110, No. 39, pp. 15644-15649 (Sep. 24, 2013).

\* cited by examiner

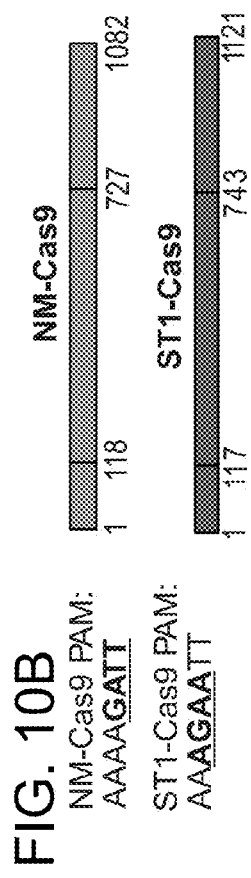
FIG. 10A
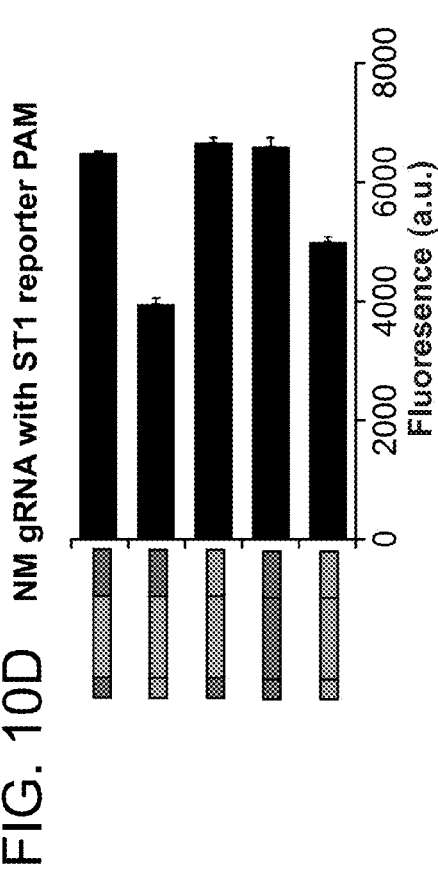
FIG. 10B
NM-Cas9 PAM: AAAAGATT
ST1-Cas9 PAM: AAAGAATT
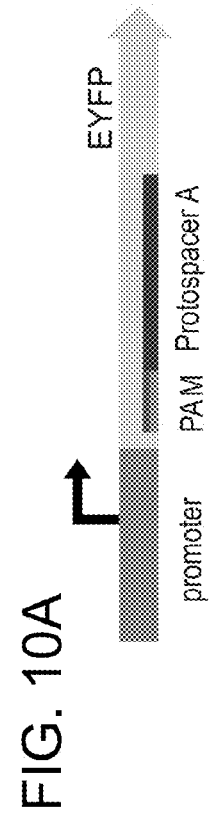
FIG. 10C NM gRNA with NM reporter PAM
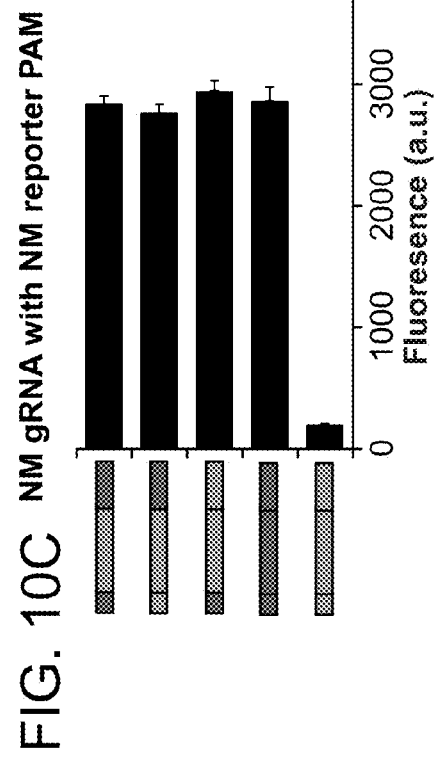
FIG. 10D NM gRNA with ST1 reporter PAM
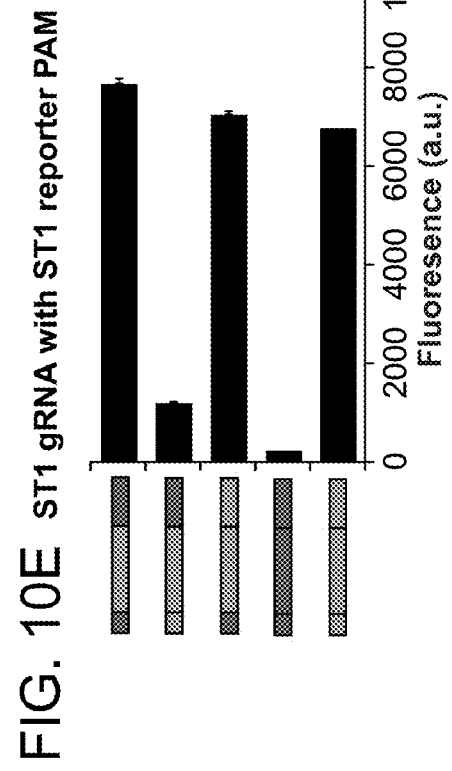
FIG. 10E ST1 gRNA with ST1 reporter PAM
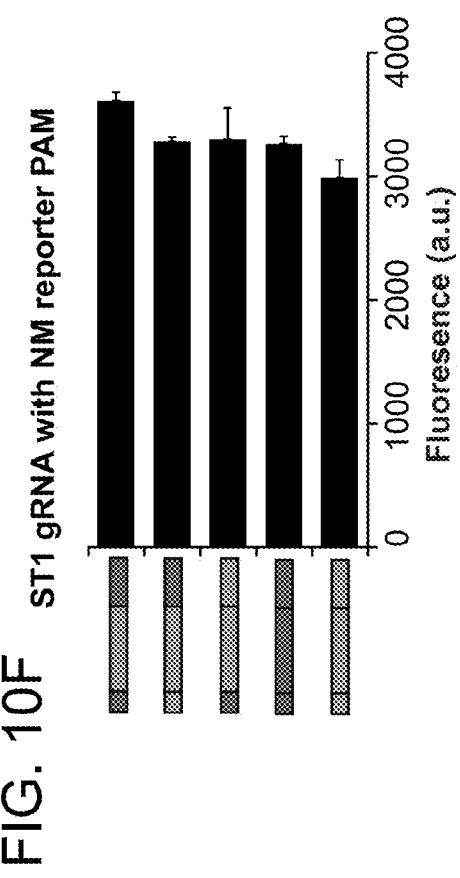
FIG. 10F ST1 gRNA with NM reporter PAM

SEQUENCE LISTING

<160> NUMBER OF SEQ ID NOS: 3

<210> SEQ ID NO 1
<211> LENGTH: 2679
<212> TYPE: DNA
<213> ORGANISM: Neisseria meningitidis

<400> SEQUENCE: 1

```
atggccgcct tcaagcccaa ccccatcaac tacatcctgg gcctggccat cggcatcgcc      60
agcgtgggct gggccatggt ggagatcgac gaggacgaga accccatctg cctgatcgac     120
ctgggtgtgc gcgtgttcga gcgcgctgag gtgcccaaga ctggtgacag tctggctatg     180
gctcgccggc ttgctcgctc tgttcggcgc cttactcgcc ggcgcgctca ccgccttctg     240
cgcgctcgcc gcctgctgaa gcgcgagggt gtgctgcagg ctgccgactt cgacgagaac     300
ggcctgatca agagcctgcc caacactcct tggcagctgc gcgctgccgc tctggaccgc     360
aagctgactc ctctggagtg gagcgccgtg ctgctgcacc tgatcaagca ccgcggctac     420
ctgagccagc gcaagaacga gggcgagacc gccgacaagg agctgggtgc tctgctgaag     480
ggcgtggccg acaacgccca cgccctgcag actggtgact ccgcactcc tgctgagctg     540 gccctgaaca agttcgagaa ggagagcggc cacatccgca accagcgcgg cgactacagc     600
cacaccttca gccgcaagga cctgcaggcc gagctgatcc tgctgttcga gaagcagaag     660
gagttcggca accccacgt gagcggcggc ctgaaggagg gcatcgagac cctgctgatg     720
acccagcgcc ccgccctgag cggcgacgcc gtgcagaaga tgtccggcgg cggttcgggc     780
gaccactacg gcaagaagaa caccgaggag aagatctacc tgcctcctat ccccgccgac     840
gagatccgca cccgtggt gctgcgcgcc ctgagccagg cccgcaaggt gatcaacggc     900
gtggtgcgcc gctacggcag ccccgcccgc atccacatcg agaccgcccg cgaggtgggc     960
aagagcttca ggaccgcaa ggagatcgag aagcgccagg aggagaaccg caaggaccgc     1020
gagaaggccg ccgccaagtt ccgcgagtac ttccccaact tcgtgggcga gcccaagagc     1080
aaggacatcc tgaagctgcg cctgtacgag cagcagcacg gcaagtgcct gtacagcggc     1140
aaggagatca acctgggccg cctgaacgag aagggctacg tggagatcgc cgctgccctg     1200
cccttcagcc gcacctggga cgacagcttc aacaacaagg tgctggtgct gggcagcgag     1260
gctcagaaca agggcaacca gacccctac gagtacttca acggcaagga caacagccgc     1320
gagtggcagg agttcaaggc ccgcgtggag accagccgct tccccgcag caagaagcag     1380
```

-continued

```
cgcatcctgc tgcagaagtt cgacgaggac ggcttcaagg agcgcaacct gaacgacacc   1440
cgctacgtga accgcttcct gtgccagttc gtggccgacc gcatgcgcct gaccggcaag   1500
ggcaagaagc gcgtgttcgc cagcaacggc cagatcacca acctgctgcg cggcttctgg   1560
ggcctgcgca aggtgcgcgc cgagaacgac cgccaccacg ccctggacgc cgtggtggtg   1620
gcctgcagca ccgtggccat gcagcagaag atcacccgct tcgtgcgcta caaggagatg   1680
aacgccttcg acggtaaaac catcgacaag gagaccggcg aggtgctgca ccagaagacc   1740
cacttccccc agccctggga gttcttcgcc caggaggtga tgatccgcgt gttcggcaag   1800
cccgacggca agcccgagtt cgaggaggcc gacacccccg agaagctgcg caccctgctg   1860
gccgagaagc tgagcagccg ccctgaggcc gtgcacgagt acgtgactcc tctgttcgtg   1920
agccgcgccc ccaaccgcaa gatgagcggt cagggtcaca tggagaccgt gaagagcgcc   1980
aagcgcctgg acgagggcgt gagcgtgctg cgcgtgcccc tgacccagct gaagctgaag   2040
gacctggaga agatggtgaa ccgcgagcgc gagcccaagc tgtacgaggc cctgaaggcc   2100
cgcctggagg cccacaagga cgacccccgcc aaggccttcg ccgagccctt ctacaagtac   2160
gacaaggccg gcaaccgcac ccagcaggtg aaggccgtgc gcgtggagca ggtgcagaag   2220
accggcgtgt gggtgcgcaa ccacaacggc atcgccgaca acgccaccat ggtgcgcgtg   2280
gacgtgttcg agaagggcga caagtactac ctggtgccca tctacagctg gcaggtggcc   2340
aagggcatcc tgcccgaccg cgccgtggtg cagggcaagg acgaggagga ctggcagctg   2400
atcgacgaca gcttcaactt caagttcagc ctgcacccca acgacctggt ggaggtgatc   2460
accaagaagg cccgcatgtt cggctacttc gccagctgcc accgcggcac cggcaacatc   2520
aacatccgca tccacgacct ggaccacaag atcggcaaga acggcatcct ggagggcatc   2580
ggcgtgaaga ccgccctgag cttccagaag taccagatcg acgagctggg caaggagatc   2640
cgcccctgcc gcctgaagaa gcgccctcct gtgcgctaa                          2679
```

<210> SEQ ID NO 2
<211> LENGTH: 3000
<212> TYPE: DNA
<213> ORGANISM: Neisseria meningitidis

<400> SEQUENCE: 2

```
atggccgcct tcaagcccaa ccccatcaac tacatcctgg gcctggccat cggcatcgcc     60
agcgtgggct gggccatggt ggagatcgac gaggacgaga accccatctg cctgatcgac    120
ctgggtgtgc gcgtgttcga gcgcgctgag gtgcccaaga ctggtgacag tctggctatg    180
gctcgccggc ttgctcgctc tgttcggcgc cttactcgcc ggcgcgctca ccgccttctg    240
cgcgctcgcc gcctgctgaa gcgcgagggt gtgctgcagg ctgccgactt cgacgagaac    300
ggcctgatca agagcctgcc caacactcct tggcagctgc gcgctgccgc tctggaccgc    360
aagctgactc ctctggagtg gagcgccgtg ctgctgcacc tgatcaagca ccgcggctac    420
ctgagccagc gcaagaacga gggcgagacc gccgacaagg agctgggtgc tctgctgaag    480
ggcgtggccg acaacgccca cgccctgcag actggtgact tccgcactcc tgctgagctg    540
gccctgaaca agttcgagaa ggagagcggc cacatccgca accagcgcgg cgactacagc    600
cacaccttca gccgcaagga cctgcaggcc gagctgatcc tgctgttcga gaagcagaag    660
gagttcggca acccccacgt gagcggcggc ctgaaggagg gcatcgagac cctgctgatg    720
acccagcgcc ccgccctgag cggcgacgcc gtgcagaaga tgctgggcca ctgcaccttc    780
gagccagccg agcccaaggc cgccaagaac acctacaccg ccgagcgctt catctggctg    840
```

```
accaagctga acaacctgcg catcctggag cagggcagcg agcgcccccc gaccgacacc    900
gagcgcgcca ccctgatgga cgagccctac cgcaagagca agctgaccta cgcccaggcc    960
cgcaagctgc tgggtctgga ggacaccgcc ttcttcaagg gcctgcgcta cggcaaggac   1020
aacgccgagc ccagcaccct gatggagatg aaggcctacc acgccatcag ccgcgccctg   1080
gagaaggagg gcctgaagga caagaagagt cctctgaacc tgagccccga gctgcaggac   1140
gagatcggca ccgccttcag cctgttcaag accgacgagg acatcaccgg ccgcctgaag   1200
gaccgcatcc agcccgagat cctggaggcc ctgctgaagc acatcagctt cgacaagttc   1260
gtgcagatca gcctgaaggc cctgcgccgc atcgtgcccc tgatggagca gggcaagcgc   1320
tacgacgagg cctgcgccga gatctacggc gaccactacg gcaagaagaa caccgaggag   1380
aagatctacc tgcctcctat ccccgccgac gagatccgca cccccgtggt gctgcgcgcc   1440
ctgagccagg cccgcaaggt gatcaacggc gtggtgcgcc gctacggcag ccccgcccgc   1500
atccacatcg agaccgcccg cgaggtgggc aagagcttca aggaccgcaa ggagatcgag   1560
aagcgccagg aggagaaccg caaggaccgc gagaaggccg ccgccaagtt ccgcgagtac   1620
ttccccaact tcgtgggcga gcccaagagc aaggacatcc tgaagctgcg cctgtacgag   1680
cagcagcacg gcaagtgctc cggcggcggt tcgcagaagt cgacgagga cggcttcaag   1740
gagcgcaacc tgaacgacac ccgctacgtg aaccgcttcc tgtgccagtt cgtggccgac   1800
cgcatgcgcc tgaccggcaa gggcaagaag cgcgtgttcg ccagcaacgg ccagatcacc   1860
aacctgctgc gcggcttctg gggcctgcgc aaggtgcgcg ccgagaacga ccgccaccac   1920
gccctggacg ccgtggtggt ggcctgcagc accgtggcca tgcagcagaa gatcacccgc   1980
ttcgtgcgct acaaggagat gaacgccttc gacggtaaaa ccatcgacaa ggagaccggc   2040
gaggtgctgc accagaagac ccacttcccc cagccctggg agttcttcgc ccaggaggtg   2100
atgatccgcg tgttcggcaa gcccgacggc aagcccgagt cgaggaggc cgacaccccc   2160
gagaagctgc gcaccctgct ggccgagaag ctgagcagcc gccctgaggc cgtgcacgag   2220
tacgtgactc ctctgttcgt gagccgcgcc cccaaccgca agatgagcgg tcagggtcac   2280
atggagaccg tgaagagcgc caagcgcctg acgagggcg tgagcgtgct gcgcgtgccc   2340
ctgacccagc tgaagctgaa ggacctggaa aagatggtga accgcgagcg cgagcccaag   2400
ctgtacgagc cctgaaggc cgcctggag gcccacaagg cgaccccgc caaggccttc   2460
gccgagccct tctacaagta cgacaaggcc ggcaaccgca cccagcaggt gaaggccgtg   2520
cgcgtggagc aggtgcagaa gaccggcgtg tgggtgcgca ccacaacgg catcgccgac   2580
aacgccacca tggtgcgcgt ggacgtgttc gagaagggcg acaagtacta cctggtgccc   2640
atctacagct ggcaggtggc caagggcatc ctgcccgacc gcgccgtggt gcagggcaag   2700
gacgaggagg actggcagct gatcgacgac agcttcaact tcaagttcag cctgcacccc   2760
aacgacctgg tggaggtgat caccaagaag gcccgcatgt tcggctactt cgccagctgc   2820
caccgcggca ccggcaacat caacatccgc atccacgacc tggaccacaa gatcggcaag   2880
aacggcatcc tggagggcat cggcgtgaag accgccctga gcttccagaa gtaccagatc   2940
gacgagctgg gcaaggagat ccgccccctg cgcctgaaga agcgccctcc tgtgcgctaa   3000
```

<210> SEQ ID NO 3
<211> LENGTH: 5064
<212> TYPE: DNA
<213> ORGANISM: Neisseria meningitidis

<400> SEQUENCE: 3

```
agctctcgaa ccccagagtc ccgctcagaa gaactcgtca agaaggcgat agaaggcgat    60
gcgctgcgaa tcgggagcgg cgataccgta aagcacgagg aagcggtcag cccattcgcc   120
gccaagctct tcagcaatat cacgggtagc caacgctatg tcctgatagc ggtccgccac   180
acccagccgg ccacagtcga tgaatccaga aaagcggcca ttttccacca tgatattcgg   240
caagcaggca tcgccatggg tcacgacgag atcctcgccg tcgggcatgc gcgccttgag   300
cctggcgaac agttcggctg gcgcgagccc ctgatgctct tcgtccagat catcctgatc   360
gacaagaccg gcttccatcc gagtacgtgc tcgctcgatg cgatgtttcg cttggtggtc   420
gaatgggcag gtagccggat caagcgtatg cagccgccgc attgcatcag ccatgatgga   480
tactttctcg gcaggagcaa ggtgagatga caggagatcc tgccccggca cttcgcccaa   540
tagcagccag tcccttcccg cttcagtgac aacgtcgagc acagctgcgc aaggaacgcc   600
cgtcgtggcc agccacgata gccgcgctgc ctcgtcctgc agttcattca gggcaccgga   660
caggtcggtc ttgacaaaaa gaaccgggcg ccctgcgct gacagccgga cacggcggc    720
atcagagcag ccgattgtct gttgtgccca gtcatagccg aatagcctct ccacccaagc   780
ggccggagaa cctgcgtgca atccatcttg ttcaatcatg cgaaacgatc ctcatcctgt   840
ctcttgatca gatcttgatc ccctgcgcca tcagatcctt ggcggcaaga aagccatcca   900
gtttactttg cagggcttcc caaccttacc agagggcgcc ccagctggca attccgacgt   960
ctaagaaacc attattatca tgacattaac ctataaaaat aggcgtatca cgaggccctt  1020
tcgtcttcac ctcgagggga caatgaaaac gttagtcatg cgcgccttg acggctagct  1080
cagtcctagg tacagtgcta gcttaatgct cgcacatagc agaactttaa agtattcgc   1140
catgttgtag ctccctttct catttcgcag tgctacaatc cgccgctatg gtcccacgta  1200
gagcatacgg aaaaaaaagt caaaagcctc cgaccggagg tcggccttac ttgctagcag  1260
agtttgtaga acgcaaaaa ggccatccgt caggatggcc ttctgcttaa tttgatgcct  1320
ggcagtttat ggcgggcgtc ctgcccgcca ccctccgggc cgttgcttcg caacgttcaa  1380
atccgctccc ggcggatttg tcctactcag gagagcgttc accgacaaac aacagataaa  1440
acgaaaggcc cagtctttcg actgagccct tcgttttatt tgatgcctgg cagttccta  1500
ctctcgcatg gggagacccc acactaccat cggcgctacg gcgtttcact tctgagttcg  1560
gcatggggtc aggtgggacc accgcgctac tgccgccagg caaattctgt tttatcagac  1620
cgcttctgcg ttctgattta atctgtatca ggctgaaaat cttctctcat ccgccaaaac  1680
agccccgtag aaaaagggac gttgatcggc acgtaagagg ttccacgata aatatctaac  1740
accgtgcgtg ttgactattt tacctctggc ggtgataatg gttgcatgta ctagaattct  1800
ttaactttaa gaaggagata tacatatgaa tcccctatgg cgaatacttt taaagtctcg  1860
taaaggagaa gaacttttca ctggagttgt cccaattctt gttgaattag atggtgatgt  1920
taatgggcac aaattttctg tcagtggaga gggtgaaggt gatgcaacat acggaaaact  1980
tacccttaaa tttatttgca ctactggaaa actacctgtt ccatggccaa cacttgtcac  2040
tactttcggt tatggtctaa atgctttgc tagatacca gatcatatga acggcatga    2100
cttttcaag agtgccatgc ccgaaggtta tgtacaggaa agaactatat ttttcaaaga  2160
tgacgggaac tacaagacac gtgctgaagt caagtttgaa ggtgataccc ttgttaatag  2220
aatcgagtta aaaggtattg attttaaaga agatggaaac attcttggac acaaattgga  2280
atacaactat aactcacaca atgtatacat catggcagac aaacaaaaga atggaatcaa  2340
```

-continued

```
agttaacttc aaaattagac acaacattga agatggaagc gttcaactag cagaccatta    2400
tcaacaaaat actccaattg gcgatggccc tgtcctttta ccagacaacc attacctgtc    2460
ctatcaatct gcccttttcga aagatcccaa cgaaaagaga gaccacatgg tccttcttga   2520
gtttgtaaca gctgctggga ttacacatgg catggatgaa ctatacaaat aagcttaacc    2580
gaagcgtttg atagttgata tcctttgcct gcggccgcaa ctagaggcat caaataaaac    2640
gaaaggctca gtcgaaagac tgggcctttc gttttatctg ttgtttgtcg gtgaacgctc    2700
tcctgagtag gacaaatccg ccgccctaga cctagggtac gggttttgct gcccgcaaac    2760
gggctgttct ggtgttgcta gtttgttatc agaatcgcag atccggcttc aggtttgccg    2820
gctgaaagcg ctatttcttc cagaattgcc atgattttt ccccacggga ggcgtcactg     2880
gctcccgtgt tgtcggcagc tttgattcga taagcagcat cgcctgtttc aggctgtcta    2940
tgtgtgactg ttgagctgta acaagttgtc tcaggtgttc aatttcatgt tctagttgct    3000 ttgtttact ggtttcacct gttctattag gtgttacatg ctgttcatct gttacattgt     3060
cgatctgttc atggtgaaca gctttaaatg caccaaaaac tcgtaaaagc tctgatgtat    3120
ctatcttttt tacaccgttt tcatctgtgc atatggacag ttttcccttt gatatctaac    3180
ggtgaacagt tgttctactt ttgtttgtta gtcttgatgc ttcactgata gatacaagag    3240
ccataagaac ctcagatcct tccgtattta gccagtatgt tctctagtgt ggttcgttgt    3300
ttttgcgtga gccatgagaa cgaaccattg agatcatgct tactttgcat gtcactcaaa    3360
aattttgcct caaaactggt gagctgaatt tttgcagtta aagcatcgtg tagtgttttt    3420
cttagtccgt tacgtaggta ggaatctgat gtaatggttg ttggtatttt gtcaccattc    3480
atttttatct ggttgttctc aagttcggtt acgagatcca tttgtctatc tagttcaact    3540
tggaaaatca acgtatcagt cgggcggcct cgcttatcaa ccaccaattt catattgctg    3600
taagtgttta aatctttact tattggtttc aaaacccatt ggttaagcct tttaaactca    3660
tggtagttat tttcaagcat taacatgaac ttaaattcat caaggctaat ctctatattt    3720
gccttgtgag ttttcttttg tgttagttct tttaataacc actcataaat cctcatagag    3780
tatttgtttt caaaagactt aacatgttcc agattatatt ttatgaattt ttttaactgg    3840
aaaagataag gcaatatctc ttcactaaaa actaattcta atttttcgct tgagaacttg    3900
gcatagtttg tccactggaa aatctcaaag cctttaacca aaggattcct gatttccaca    3960
gttctcgtca tcagctctct ggttgcttta gctaatacac cataagcatt ttccctactg    4020
atgttcatca tctgagcgta ttggttataa gtgaacgata ccgtccgttc tttccttgta    4080
gggttttcaa tcgtggggtt gagtagtgcc acacagcata aaattagctt ggtttcatgc    4140
tccgttaagt catagcgact aatcgctagt tcatttgctt tgaaaacaac taattcagac    4200
atacatctca attggtctag gtgattttaa tcactatacc aattgagatg ggctagtcaa    4260
tgataattac tagtccttttt cctttgagtt gtgggtatct gtaaattctg ctagaccttt   4320
gctggaaaac ttgtaaattc tgctagaccc tctgtaaatt ccgctagacc tttgtgtgtt    4380
ttttttgttt atattcaagt ggttataatt tatagaataa agaagaata aaaaagata      4440 aaagaatag atcccagccc tgtgtataac tcactacttt agtcagttcc gcagtattac     4500
aaaaggatgt cgcaaacgct gtttgctcct ctacaaaaca gaccttaaaa ccctaaaggc    4560
ttaagtagca ccctcgcaag ctcgggcaaa tcgctgaata ttccttttgt ctccgaccat    4620
caggcacctg agtcgctgtc tttttcgtga cattcagttc gctgcgctca cggctctggc    4680
```

| | | | | | | |
|---|---|---|---|---|---|---|
| agtgaatggg | ggtaaatggc | actacaggcg | cctttatgg | attcatgcaa | ggaaactacc | 4740 |
| cataatacaa | gaaaagcccg | tcacgggctt | ctcagggcgt | tttatggcgg | gtctgctatg | 4800 |
| tggtgctatc | tgactttttg | ctgttcagca | gttcctgccc | tctgattttc | cagtctgacc | 4860 |
| acttcggatt | atcccgtgac | aggtcattca | gactggctaa | tgcacccagt | aaggcagcgg | 4920 |
| tatcatcaac | aggcttaccc | gtcttactgt | ccctagtgct | tggattctca | ccaataaaaa | 4980 |
| acgcccggcg | gcaaccgagc | gttctgaaca | aatccagatg | gagttctgag | gtcattactg | 5040 |
| gatctatcaa | caggagtcca | agcg | | | | 5064 |

MUTANT CAS9 PROTEINS

RELATED APPLICATION

This application is a continuation application which claims priority to U.S. patent application Ser. No. 16/440,241, filed on Jun. 13, 2019, which is a continuation application which claims priority to U.S. patent application Ser. No. 16/157,481, filed on Oct. 11, 2018, which is a divisional application which claims priority to U.S. patent application Ser. No. 15/037,696, filed on May 19, 2016, which is a National Stage Application under 35 U.S.C. 371 of co-pending PCT application PCT/US14/66375, filed Nov. 19, 2014; which claims the benefit of U.S. provisional application 61/906,374, filed Nov. 19, 2013 each of which are hereby incorporated by reference in their entireties.

STATEMENT OF GOVERNMENT INTERESTS

This invention was made with government support under Grant No. HG005550 awarded by the National Institutes of Health. The government has certain rights in the invention

BACKGROUND

Bacterial and archaeal CRISPR-Cas systems rely on short guide RNAs in complex with Cas proteins to direct degradation of complementary sequences present within invading foreign nucleic acid. See Deltcheva, E. et al. CRISPR RNA maturation by trans-encoded small RNA and host factor RNase III. *Nature* 471, 602-607 (2011); Gasiunas, G, Barrangou, R., Horvath, P. & Siksnys, V. Cas9-crRNA ribonucleoprotein complex mediates specific DNA cleavage for adaptive immunity in bacteria. *Proceedings of the National Academy of Sciences of the United States of America* 109, E2579-2586 (2012); Jinek, M. et al. A programmable dual-RNA-guided DNA endonuclease in adaptive bacterial immunity. *Science* 337, 816-821 (2012); Sapranauskas, R. et al. The *Streptococcus thermophilus* CRISPR/Cas system provides immunity in *Escherichia coli. Nucleic acids research* 39, 9275-9282 (2011); and Bhaya, D., Davison, M. & Barrangou, R. CRISPR-Cas systems in bacteria and archaea: versatile small RNAs for adaptive defense and regulation. *Annual review of genetics* 45, 273-297 (2011). A recent in vitro reconstitution of the *S. pyogenes* type II CRISPR system demonstrated that crRNA ("CRISPR RNA") fused to a normally trans-encoded tracrRNA ("trans-activating CRISPR RNA") is sufficient to direct Cas9 protein to sequence-specifically cleave target DNA sequences matching the crRNA. Expressing a gRNA homologous to a target site results in Cas9 recruitment and degradation of the target DNA. See H. Deveau et al., Phage response to CRISPR-encoded resistance in *Streptococcus thermophilus. Journal of Bacteriology* 190, 1390 (February, 2008).

Cas9 is a DNA nuclease that can be programmed to target nearly any region of a genome by expressing a guide RNA (gRNA) that contains a motif that recruits Cas9 and 20 basepairs of complementarity to a region of the genome where targeting is desired. All characterized and putative Cas9 family members are several kilobases in size (>3,000 basepairs) with the smallest functionally validated member NM-Cas9 (*Neisseria meningitides* Cas9) being 3,249 basepairs in size. The large size of this protein limits its potential for biotechnology and therapeutic applications due to difficulties of delivery and manipulation.

SUMMARY

Aspects of the present disclosure are directed to an RNA guided DNA binding protein of a Type II CRISPR System that binds to the DNA and is guided by the one or more RNAs which has been engineered to omit portions of the protein while still functioning as an RNA guided DNA binding nuclease that can bind to target DNA and create a double stranded break in target DNA. According to one aspect, the RNA guided DNA binding protein of a Type II CRISPR System is a Cas9 protein.

Aspects of the present disclosure are directed to an RNA guided DNA binding protein of a Type II CRISPR System which has been engineered to omit portions of the protein while still functioning as an RNA guided DNA binding nickase that can bind to target DNA and create a single stranded break or nick in target DNA. According to one aspect, the RNA guided DNA binding protein of a Type II CRISPR System is a Cas9 protein.

Aspects of the present disclosure are directed to an RNA guided DNA binding protein of a Type II CRISPR System which has been engineered to omit portions of the protein while still functioning as an RNA guided DNA binding protein which is nuclease null, that is, the RNA guided DNA binding protein lacks nuclease activity. According to one aspect, the RNA guided DNA binding protein of a Type II CRISPR System is a Cas9 protein.

According to one aspect, portions of an RNA guided DNA binding protein are identified for deletion by identifying within a population of species of the RNA guided DNA binding protein sequences which are not well conserved or are otherwise highly divergent within a particular RNA guided DNA binding protein family and/or protein sequences between boundaries between low and high conservation referred to herein as "conservation edges" within a particular RNA guided DNA binding protein family According to this aspect, amino acid sequences within a DNA binding protein, such as an RNA guided DNA binding protein, such as Cas9, are identified as having either high conservation or low conservation using methods described herein and as are known to those of skill in the art. According to one aspect, amino acid sequences of high conservation and amino acid sequences of low conservation are adjacent, such as immediately adjacent, to one another within the protein sequence of the DNA binding protein as a whole. The amino acid sequences of high conservation and the amino acid sequences of low conservation are distinguished by an amino acid which separates an amino acid sequence of high conservation from an amino acid sequence of low conservation. In this manner, the amino acid which separates an amino acid sequence of high conservation from an amino acid sequence of low conservation is referred to herein as an "edge amino acid" or a "conservation edge" to the extent that it is at an edge or terminal portion of either an amino acid sequence of high conservation or an amino acid sequence of low conservation. Accordingly, the methods of the present disclosure contemplate identifying an amino acid which separates an amino acid sequence of high conservation from an amino acid sequence of low conservation or otherwise distinguishes an amino acid sequence of high conservation from an amino acid sequence of low conservation. Such an amino acid is referred to herein as an "edge amino acid." According to this aspect, a pair of edge amino acids may flank or bound on either end an amino acid sequence of high conservation. Likewise, a pair of edge amino acids may flank or bound on either end an amino acid sequence of low conservation. Still according to this aspect, one exemplary embodiment relates to the identification within the protein sequence of a DNA binding protein as a whole, adjacent amino acid sequences of high conservation and amino acid sequences of low conservation. In particular, one exemplary embodiment relates to the identification within the protein sequence of a DNA binding protein as a whole, sequences of high conservation in tandem or in series with sequences of low conservation, and in particular, a sequence of high conservation (HC) bounded on either end by a sequence of low conservation (LC) or alternatively a sequence of low conservation (LC) bounded on either end by a sequence of high conservation (HC). In this manner, exemplary tandem sequences or sequences in series identified by the methods described herein may be schematically depicted as LC-HC-LC or HC-LC-HC. According to this aspect, a middle sequence of either high conservation or low conservation is bounded by flanking sequences of either low conservation or high conservation, respectively. In the exemplary tandem sequence LC-HC-LC, a pair of edge amino acids distinguish or separate the amino acid sequence of high conservation (HC) from the two flanking amino acid sequences of low conservation (LC) which are on either end of or otherwise bound the amino acid sequence of high concentration. In the exemplary tandem sequence HC-LC-HC, a pair of edge amino acids distinguish or separate the amino acid sequence of low conservation (LC) from the two flanking amino acid sequences of high conservation (HC) which are on either end of or otherwise bound the amino acid sequence of low conservation. When such an exemplary tandem sequence is identified using the methods described herein, whether the middle sequence is either an amino acid sequence of high conservation or an amino acid sequence of low conservation, the middle sequence is removed to create a mutant DNA binding protein according to the methods described herein which retains DNA binding activity and which is smaller in size compared to the wild type DNA binding protein. The edge amino acids define the middle sequence to be removed by flanking the middle sequence or otherwise separating the middle sequence from adjacent sequences in series to create the mutant DNA binding protein. According to certain aspects of the present disclosure, a middle sequence in the tandem sequences can be removed regardless of whether the middle sequence is an amino acid sequence of high conservation or an amino acid sequence of low conservation insofar as the mutant DNA binding protein retains useful DNA binding protein activity.

In order to identify sequences which are not well conserved or protein sequences between conservation edges within the context of this disclosure, an alignment was obtained from PFAM or otherwise created from a collection of sequences resulting from a database search of Cas9 homologs. This alignment was computationally conditioned and the conservation was calculated as the per position (relative) entropy of amino acid frequencies. The sequences are then removed from the RNA guided DNA binding protein to produce a mutant.

According to one aspect, in order to identify regions within the multi-domain Cas9 protein that may be amenable to deletion, a bioinformatics approach is used to identify potential domain boundaries in the Cas9 proteins. A multiple sequence alignment is created by re-aligning Cas9 sequences in the PFAM database (PF13395) using MUSCLE, and the alignment is computationally conditioned for diversity and full-length sequences. The sequence conservation is calculated as the relative entropy of observed amino acid frequencies with respect to the average frequencies across all genes in *Escherichia coli*. A multi-scale edge filter (difference of Gaussians (DoG) band-pass filter) is applied to the conservation profile to assign potential protein domain boundaries referred to herein as conservation edges. Regions in between the conservation edges are selected for deletion in the first iteration of deletion mutants.

According to certain aspects, the present disclosure describes synthetic NM-Cas9 deletion mutants that are smaller in size yet retain near wild-type protein activity. The synthetic NM-Cas9 deletion mutants can be used to bind to DNA as a co-localization complex with guide RNA in a cell and create a double stranded break, a single stranded break or to locate an effector group near target DNA of interest to perform a desired function.

According to certain aspects an alignment-based domain detection method is provided to identify regions of a DNA binding protein, such as Cas9, that are dispensable for binding to DNA, and which can be removed to form a mutant DNA binding protein that is smaller in size compared to the wild type DNA binding protein. According to methods described herein, minimized Cas9 variants are generated that show robust activity in bacteria and human cells. According to aspects described herein, mutant functional DNA binding protein variants, such as mutant functional Cas9 variants, which are smaller than wild type DNA binding proteins, are provided.

According to certain aspects, exemplary DNA binding proteins include Cas9 orthologs such as *Neisseria meningitidis* Cas9 (NM, GI: 218767588) and *Streptococcus thermophilus* Cas9 (ST1, GI: 116627542) which have been shown to function in both prokaryotes and higher eukaryotes. See Hou, Z. et al. Efficient genome engineering in human pluripotent stem cells using Cas9 from *Neisseria meningitidis. Proceedings of the National Academy of Sciences of the United States of America* 110, 15644-15649, doi:10.1073/pnas.1313587110 (2013) hereby incorporated by reference in its entireties.

These exemplary Cas9 orthologs are smaller in gene size compared to *Streptococcus pyogenes* Cas9 (SP, GI: 13622193), i.e. about 3200 versus 4100 base pairs. Aspects of the present disclosure are therefore directed to reducing the size of a Cas9 DNA binding protein so as to increase the efficiency with which the Cas9 DNA binding protein can be delivered, particularly using viral packaging technologies where gene length can greatly influence viral titer. See Kumar, M., Keller, B., Makalou, N. & Sutton, R. E. Systematic determination of the packaging limit of lentiviral vectors. *Human gene therapy* 12, 1893-1905, doi:10.1089/104303401753153947 (2001); Wu, Z., Yang, H. & Colosi, P. Effect of genome size on AAV vector packaging. *Molecular therapy: the journal of the American Society of Gene Therapy* 18, 80-86, doi:10.1038/mt.2009.255 (2010); and Gelinas, C. & Temin, H. M. Nondefective spleen necrosis virus-derived vectors define the upper size limit for packaging reticuloendotheliosis viruses. *Proceedings of the National Academy of Sciences of the United States of America* 83, 9211-9215 (1986) each of which is hereby incorporated in its entirety.

Synthetically reducing the size of Cas9 genes allow for more complex regulatory systems and functional domains to be packaged within single vectors. According to an additional aspect, methods are provided to synthetically alter PAM specificity allowing for the generation of smaller Cas9 variants with increased targeting potential.

According to certain aspects, methods are provided for making Cas9 chimera by exchanging the C-terminal domain of a first species of Cas9 with the C-terminal domain of a second species of Cas9. According to one aspect, the present disclosure provides domain exchange Cas9 chimera, such as a functional NM-ST1-Cas9 chimera, by exchanging the C-terminal domain of NM with ST1. The chimeric Cas9 protein exhibits ST1 guideRNA and PAM specificity.

According to one aspect, the cell is a prokaryotic cell or a eukaryotic cell. According to one aspect, the cell is a bacterial cell, a yeast cell, a plant cell or an animal cell. According to one aspect, the cell is a mammalian cell.

According to one aspect, the RNA is between about 10 to about 500 nucleotides. According to one aspect, the RNA is between about 20 to about 100 nucleotides.

According to one aspect, the one or more RNAs is a guide RNA. According to one aspect, the one or more RNAs is a crRNA. According to one aspect, the one or more RNAs is a tracrRNA. According to one aspect, the one or more RNAs is a tracrRNA-crRNA fusion.

According to one aspect, the target DNA is genomic DNA, mitochondrial DNA, viral DNA, conjugatable element or exogenous DNA.

According to one aspect, the RNA guided DNA binding protein is of a Type II CRISPR System that binds to the DNA and is guided by the one or more RNAs. According to one aspect, the RNA guided DNA binding protein is a Cas9 protein that binds to the DNA and is guided by the one or more RNAs.

Further features and advantages of certain embodiments of the present invention will become more fully apparent in the following description of embodiments and drawings thereof, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawings in which:

FIG. 10A is directed to NM-ST1 domain swap analysis as determined by a transcriptional repression assay and in particular, design of NM and ST1 transcriptional reporters with the sequence of the NM or ST1 specific PAM illustrated. FIG. 10B is a schematic depicting outline of NM and ST1 Cas9 with the location of the amino acid swap points noted. FIG. 10C-10F are graphs of fluorescence for NM-ST1 nuclease null domain exchange mutants expressed in conjunction with guideRNAs particular to NM (FIG. 10C and FIG. 10D) or ST1 Cas9 (FIG. 10E and FIG. 10F), along with reporters with PAM sequences specific to either NM (FIG. 10C and FIG. 10F) or ST1 Cas9 (FIG. 10D and FIG. 10E). Data represent mean±standard deviation (n=4).

DETAILED DESCRIPTION

Figure 1:
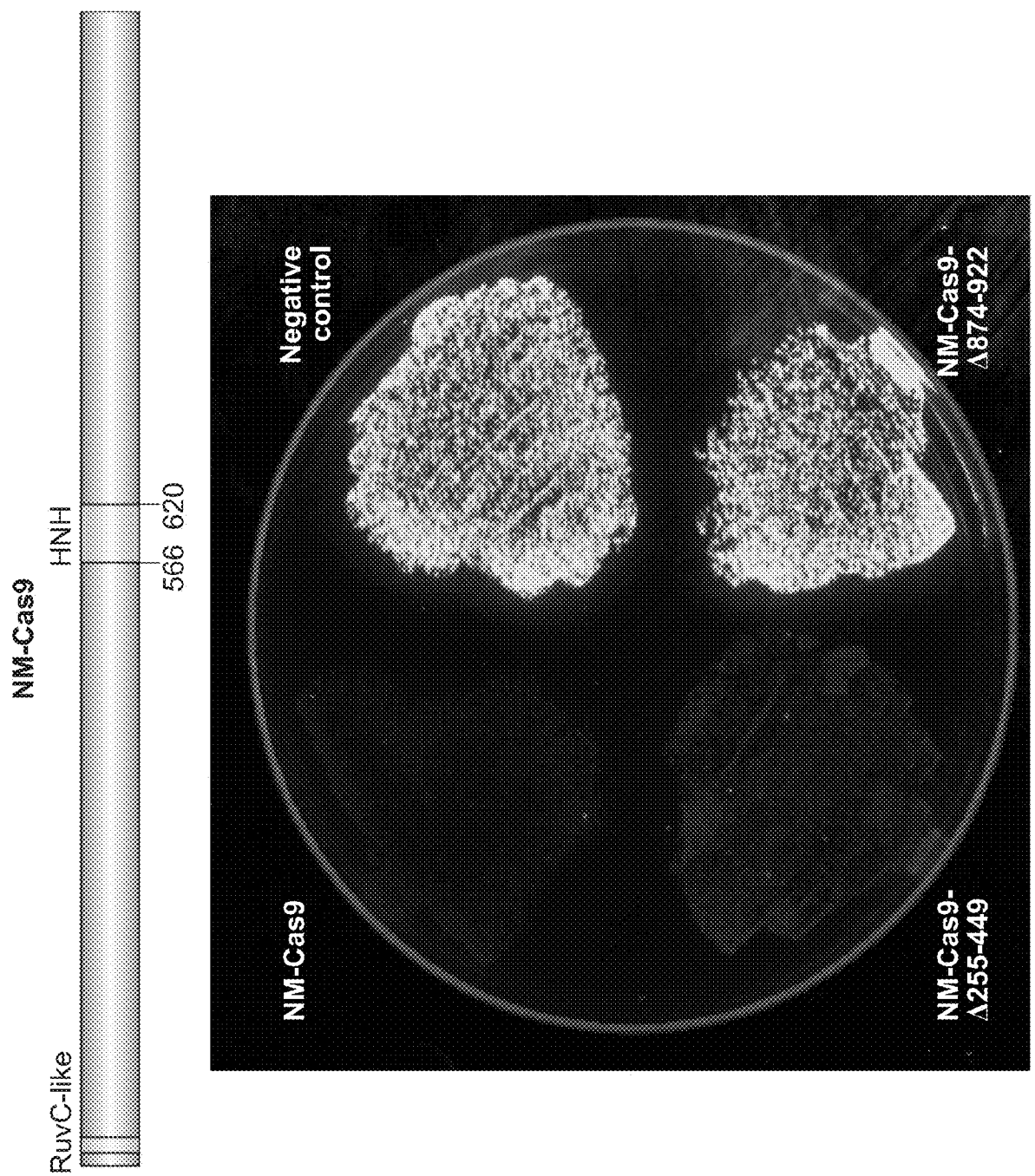
FIG. 1 is an image in which E. coli cells contain a YFP reporter for NM-Cas9 activity and are transformed with various NM-Cas9 nuclease null genes. In the absence of NM-Cas9, the cells are fluorescent (upper right quadrant-Negative control) and in the presence of full length nuclease null NM-Cas9 the cells are non-fluorescent (upper left quadrant-Positive control). Two of the generated NM-Cas9 deletions are shown, NM-Cas9-Δ255-449 shows near wild-type levels of repression (bottom left quadrant) and NM-Cas9-Δ874-922 shows lack of most DNA binding capacity (bottom right quadrant).

Embodiments of the present invention are directed to mutant RNA guided DNA binding proteins of the Type II CRISPR system. Such mutants are created by removing sequences that are not well conserved or are otherwise highly divergent among species within a genus of RNA guided DNA binding proteins of the Type II CRISPR system. According to one aspect, the sequences of species within a family of RNA guided DNA binding proteins are aligned and sequences of low conservation or sequences between conservation edges are determined. These sequences are then deleted from a particular RNA guided DNA binding protein. Exemplary RNA guided DNA binding proteins include Cas9 proteins present, for example, in Type II CRISPR systems. Such Cas9 proteins and Type II CRISPR systems are well documented in the art. See Makarova et al., *Nature Reviews, Microbiology*, Vol. 9, June 2011, pp. 467-477. The mutant DNA binding proteins described herein can be used to make double stranded cuts in target DNA, single stranded cuts in target DNA or to bind to target DNA in a manner to locate an effector group near the target DNA such that that effector group can interact with the target DNA. Such effector groups include activators, repressors or epigenetic modifiers known to those of skill in the art.

Exemplary DNA binding proteins having nuclease activity function to nick or cut double stranded DNA. Such nuclease activity may result from the DNA binding protein having one or more polypeptide sequences exhibiting nuclease activity. Such exemplary DNA binding proteins may have two separate nuclease domains with each domain responsible for cutting or nicking a particular strand of the double stranded DNA. Exemplary polypeptide sequences having nuclease activity known to those of skill in the art include the McrA-HNH nuclease related domain and the RuvC-like nuclease domain. Accordingly, exemplary DNA binding proteins are those that in nature contain one or more of the McrA-HNH nuclease related domain and the RuvC-like nuclease domain.

According to one aspect, a DNA binding protein having two or more nuclease domains may be modified or altered to inactivate all but one of the nuclease domains. Such a modified or altered DNA binding protein is referred to as a DNA binding protein nickase, to the extent that the DNA binding protein cuts or nicks only one strand of double stranded DNA. When guided by RNA to DNA, the DNA binding protein nickase is referred to as an RNA guided DNA binding protein nickase.

An exemplary DNA binding protein is an RNA guided DNA binding protein of a Type II CRISPR System. An exemplary DNA binding protein is a Cas9 protein.

In *S. pyogenes*, Cas9 generates a blunt-ended double-stranded break 3 bp upstream of the protospacer-adjacent motif (PAM) via a process mediated by two catalytic domains in the protein: an HNH domain that cleaves the complementary strand of the DNA and a RuvC-like domain that cleaves the non-complementary strand. See Jinke et al., *Science* 337, 816-821 (2012) hereby incorporated by reference in its entirety. Cas9 proteins are known to exist in many Type II CRISPR systems including the following as identified in the supplementary information to Makarova et al., *Nature Reviews, Microbiology*, Vol. 9, June 2011, pp. 467-477: *Methanococcus maripaludis* C7; *Corynebacterium diphtheriae*; *Corynebacterium efficiens* YS-314; *Corynebacterium glutamicum* ATCC 13032 Kitasato; *Corynebacterium glutamicum* ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1; *Rhodococcus opacus* B4 uid36573; *Acidothermus cellulolyticus* 11B; *Arthrobacter chlorophenolicus* A6; *Kribbella flavida* DSM 17836 uid43465; *Thermomonospora curvata* DSM 43183; *Bifidobacterium dentium* Bd1; *Bifidobacterium longum* DJO10A; *Slackia heliotrinireducens* DSM 20476; *Persephonella marina* EX H1; *Bacteroides fragilis* NCTC 9434; *Capnocytophaga ochracea* DSM 7271; *Flavobacterium psychrophilum* JIP02 86; *Akkermansia muciniphila* ATCC BAA 835; *Roseiflexus castenholzii* DSM 13941; *Roseiflexus* RS1; *Synechocystis* PCC6803; *Elusimicrobium minutum* Pei191; uncultured Termite group 1 bacterium phylotype Rs D17; *Fibrobacter succinogenes* S85; *Bacillus cereus* ATCC 10987; *Listeria innocua*; *Lactobacillus casei*; *Lactobacillus rhamnosus* GG; *Lactobacillus salivarius* UCC118; *Streptococcus agalactiae* A909; *Streptococcus agalactiae* NEM316; *Streptococcus agalactiae* 2603; *Streptococcus dysgalactiae equisimilis* GGS 124; *Streptococcus equi zooepidemicus* MGCS10565; *Streptococcus gallolyticus* UCN34 uid46061; *Streptococcus gordonii Challis* subst CH1; *Streptococcus mutans* NN2025 uid46353; *Streptococcus mutans*; *Streptococcus pyogenes*M1 GAS; *Streptococcus pyogenes* MGAS5005; *Streptococcus pyogenes* MGAS2096; *Streptococcus pyogenes* MGAS9429; *Streptococcus pyogenes* MGAS10270; *Streptococcus pyogenes* MGAS6180; *Streptococcus pyogenes* MGAS315; *Streptococcus pyogenes* SSI-1; *Streptococcus pyogenes* MGAS10750; *Streptococcus pyogenes* NZ131; *Streptococcus thermophiles* CNRZ1066; *Streptococcus thermophiles* LMD-9; *Streptococcus thermophiles* LMG 18311; *Clostridium botulinum* A3 Loch Maree; *Clostridium botulinum* B Eklund 17B; *Clostridium botulinum* Ba4 657; *Clostridium botulinum* F Langeland; *Clostridium cellulolyticum* H10; *Finegoldia magna* ATCC 29328; *Eubacterium rectale* ATCC 33656; *Mycoplasma gallisepticum*; *Mycoplasma mobile* 163K; *Mycoplasma penetrans*; *Mycoplasma synoviae* 53; *Streptobacillus moniliformis* DSM 12112; *Bradyrhizobium* BTAi1; *Nitrobacter hamburgensis* X14; *Rhodopseudomonas palustris* BisB18; *Rhodopseudomonas palustris* BisB5; *Parvibaculum lavamentivorans* DS-1; *Dinoroseobacter shibae* DFL 12; *Gluconacetobacter diazotrophicus* Pal 5 FAPERJ; *Gluconacetobacter diazotrophicus* Pal 5 JGI; *Azospirillum* B510 uid46085; *Rhodospirillum rubrum* ATCC 11170; *Diaphorobacter* TPSY uid29975; *Verminephrobacter eiseniae* EF01-2; *Neisseria meningitides* 053442; *Neisseria meningitides* alpha14; *Neisseria meningitides* Z2491; *Desulfovibrio salexigens* DSM 2638; *Campylobacter jejuni doylei* 269 97; *Campylobacter jejuni* 81116; *Campylobacter jejuni*; *Campylobacter lari* RM2100; *Helicobacter hepaticus*; *Wolinella succinogenes*; *Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida*; *Francisella tularensis novicida* U112; *Francisella tularensis holarctica*; *Francisella tularensis* FSC 198; *Francisella tularensis tularensis*; *Francisella tularensis* WY96-3418; and *Treponema denticola* ATCC 35405. Accordingly, aspects of the present disclosure are directed to a mutant of a Cas9 protein present in a Type II CRISPR system, such as any one of the species identified above. An exemplary Cas9 protein is that found in Neisseria meningitides, such as Neisseria meningitides 053442; Neisseria meningitides alpha14; Neisseria meningitides Z2491.

Cells according to the present disclosure include any cell into which foreign nucleic acids can be introduced and expressed as described herein. It is to be understood that the basic concepts of the present disclosure described herein are not limited by cell type. Cells according to the present disclosure include eukaryotic cells, prokaryotic cells, animal cells, plant cells, fungal cells, archael cells, eubacterial cells and the like. Cells include eukaryotic cells such as yeast cells, plant cells, and animal cells. Particular cells include mammalian cells. Particular cells include stem cells, such as pluripotent stem cells, such as human induced pluripotent stem cells.

Target nucleic acids include any nucleic acid sequence to which a mutant RNA guided DNA binding protein nuclease can be useful to nick or cut. Target nucleic acids include genes. For purposes of the present disclosure, DNA, such as double stranded DNA, can include the target nucleic acid and a co-localization complex can bind to or otherwise co-localize with the DNA at or adjacent or near the target nucleic acid and in a manner in which the co-localization complex may have a desired effect on the target nucleic acid. Such target nucleic acids can include endogenous (or naturally occurring) nucleic acids and exogenous (or foreign) nucleic acids. One of skill based on the present disclosure will readily be able to identify or design guide RNAs and mutant Cas9 proteins which co-localize to a DNA including a target nucleic acid. DNA includes genomic DNA, mitochondrial DNA, viral DNA, a conjugatable element or exogenous DNA.

Foreign nucleic acids (i.e. those which are not part of a cell's natural nucleic acid composition) may be introduced into a cell using any method known to those skilled in the art for such introduction. Such methods include transfection, transduction, viral transduction, microinjection, lipofection, nucleofection, nanoparticle bombardment, transformation, conjugation and the like. One of skill in the art will readily understand and adapt such methods using readily identifiable literature sources.

According to one aspect, the genetic material required to encode a Cas9 protein is reduced by deleting portions of the Cas9 protein which are not well conserved or otherwise diverge within species within a family of Cas9 or are between conservation edges within species within a family of Cas9. By reducing the size of the nucleic acid required to encode a functioning Cas9, additional nucleic acids can be included with a vector designed to deliver the Cas9, such as nucleic acids encoding guide RNA or regulatory elements or effector domains. If one uses the smallest characterized Cas9 family member, ~4,500 kilobases of DNA will be required to encode for the necessary genetic elements (Cas9 protein and gRNA) in order to properly localize Cas9 to the desired genomic locus. At ~4,500 basepairs Cas9 is near the size limit for packaging within AAV based viral vector (which is a regulatory approved viral vector in Europe.) Further, some of the first transcriptional and epigenetic effector domains to be fused to programmable DNA binding proteins are greater than 2,000 basepairs and thus far out of the packaging limit for AAV vectors and approaching the limit of lentiviral packaging systems (~8,000 basepairs) once fused to Cas9.

The following examples are set forth as being representative of the present disclosure. These examples are not to be construed as limiting the scope of the present disclosure as these and other equivalent embodiments will be apparent in view of the present disclosure, figures and accompanying claims.

Example I

Mutant Cas9

To overcome the issues of large gene size encoding Cas9, a targeted deletion is carried out of various regions within one of the smallest characterized Cas9 family member NM-Cas9 (Neisseria meningitides Cas9). NM-Cas9 is 3,249 bp in size. Requirements for targeting to the genome and the residues involved in nuclease activity are determined. To generate versions of NM-Cas9 which are smaller in size, an alignment of Cas9 proteins was generated and contiguous stretches of low conservation or stretches between conservation edges were identified for deletion. Several regions of interest were identified and selectively removed from NM-Cas9 which was then assessed for function by using a Cas9 repressor assay. In the assay, a variant of NM-Cas9 was used that lacks nuclease activity but is able to be targeted to the 5' region of a reporter gene. If NM-Cas9 is able to bind to the reporter gene it will repress transcription and in the case of a fluorescent reporter, the cells will appear non-fluorescent.

Cas9 alignment and deletion prediction: Full length sequences of Cas9 homologs were obtained either from the PFAM database or from a database search such as jackHMMER (R. D. Finn, J. Clements, S. R. Eddy, Nucleic Acids Research (2011) Web Server Issue 39:W29-W37 hereby incorporated by reference in its entirety). In case the collection of sequences is not aligned, an alignment is created using an alignment algorithm such as CLUSTALW (Sievers F, Wilm A, Dineen D G, Gibson T J, Karplus K, Li W, Lopez R, McWilliam H, Remmert M, Söding J, Thompson J D, Higgins D G (2011) hereby incorporated by reference in its entirety), or equivalent. The alignment was computationally cut to the positions of the sequence of interest and conditioned to diminish alignment bias (e.g. sequences with a greater than 95% pairwise identity were removed). Conservation is calculated as the entropy or relative entropy of amino acid frequencies per position, taking into account the amount of amino acids and gaps at that position. Deletions are targeted towards regions of low conservation or between conservation edges. In iterations with experimental verification, the deletions are expanded or shifted.

Deletion construction and characterization: Bacterial plasmids expressing nuclease null NM-Cas9 were previously generated as described in Esvelt, K. M., Mali, P., Braff, J. L., Moosburner, M., Yaung, S. J., and Church, G. M. (2013) Nat Methods 10, 1116-1121 hereby incorporated by reference in its entirety. To create targeted deletions within NM-Cas9, Gibson assembly was employed as described in Gibson, D. G., Young, L., Chuang, R. Y., Venter, J. C., Hutchison, C. A., 3rd, and Smith, H. O. (2009) Nat Methods 6, 343-345 hereby incorporated by reference in its entirety. Primers containing overlapping complementarily and which are designed to remove targeted regions within NM-Cas9 along with inserting a SGGGS linker were purchased and used in PCR reactions. PCR fragments were gel purified, assembled in vitro using Gibson assembly and transformed into E. coli. Clones were sequence verified and tested using a modified form of previously generated NM-Cas9 reporter plasmids (See (2013) *Nat Methods* 10, 1116-1121) in which a single plasmid (instead of two) contains the NM-Cas9 spacer, targeted protospacer and YFP reporter for NM-Cas9 activity. Briefly, in this assay cells are co-transformed with synthetic NM-Cas9 variants and the reporter plasmid. The doubly transformed cells are then grown up at 37° C., and the amount of YFP fluorescence is measured using a fluorescence plate reader and compared to cells that are transformed with a control plasmid with wild-type nuclease null NM-Cas9 and the reporter plasmid.

The below sequences are for the two largest NM-Cas9 single deletion mutants that retained near wild-type levels of activity as determined by the YFP reporter assay. The sequence of the SGGGS linker which replaces the deleted regions within NM-cas9 is shown in CAPS.

NM-Cas9-Δ255-449

[SEQ ID NO: 1]

```
atggccgccttcaagcccaaccccatcaactacatcctgggcctggccatcggcatcgccagcgtgggctgggccatggtggagatcgacgaggacg
agaacccatctgcctgatcgacctgggtgtgcgcgtgttcgagcgcgctgaggtgcccaagactggtgacagtctggctatggctcgccggcttgctc
gctctgttcggcgccttactcgccggcgcgctcaccgccttctgcgcgctcgccgcctgctgaagcgcgagggtgtgctgcaggctgccgacttcgacg
agaacggcctgatcaagagcctgcccaacactccttggcagctgcgcgctgccgctctggaccgcaagctgactcctctggagtggagcgccgtgctg
ctgcacctgatcaagcaccgcggctacctgagccagcgcaagaacgagggcgagaccgccgacaaggagctgggtgctctgctgaagggcgtggc
cgacaacgcccacgccctgcagactggtgacttccgcactcctgctgagctggccctgaacaagttcgagaaggagagcggccacatccgcaaccag
cgcggcgactacagccacaccttcagccgcaaggacctgcaggccgagctgatcctgctgttcgagaagcagaaggagttcggcaaccccacgtga
gcggcggcctgaaggagggcatcgagaccctgctgatgacccagcgccccgccctgagcggcgacgccgtgcagaagatgTCCGGCGGC
GGTTCGggcgaccactacgcaagaagaacaccgaggagaagatctacctgcctcctatccccgccgacgagatccgcaaccccgtggtgctg
cgcgccctgagccaggcccgcaaggtgatcaacggcgtggtgcgccgctacggcagcccgcccgcatccacatcgagaccgcccgcgaggtggg
caagagcttcaaggaccgcaaggagatcgagaagcgccaggaggagaaccgcaaggaccgcgagaaggccgccgccaagttccgcgagtacttc
cccaacttcgtgggcgagcccaagagcaaggacatcctgaagctgcgcctgtacgagcagcagcacggcaagtgcctgtacagcggcaaggagatc
aacctgggccgcctgaacgagaagggctacgtggagatcgccgctgccctgcccttcagccgcacctgggacgacagcttcaacaacaaggtgctgg
tgctgggcagcgaggctcagaacaagggcaaccagacccctacgagtacttcaacggcaaggacaacagccgcgagtggcaggagttcaaggcc
cgcgtggagaccagccgcttcccccgcagcaagaagcagcgcatcctgctgcagaagttcgacgaggacggcttcaaggagcgcaacctgaacgac
acccgctacgtgaaccgcttcctgtgccagttcgtggccgaccgcatgcgcctgaccggcaagggcaagaagcgcgtgttcgccagcaacggccaga
tcaccaacctgctgcgcggcttctggggcctgcgcaaggtgcgcgccgagaacgaccgccaccacgccctggacgccgtggtggtggcctgcagca
ccgtggccatgcagcagaagatcacccgcttcgtgcgctacaaggagatgaacgccttcgacggtaaaaccatcgacaaggagaccggcgaggtgct
gcaccagaagacccacttccccccagccctgggagttcttcgcccaggaggtgatgatccgcgtgttcggcaagcccgacggcaagcccgagttcgag
gaggccgacaccccgagaagctgcgcaccctgctggccgagaagctgagcagccgccctgaggccgtgcacgagtacgtgactcctctgttcgtga
gccgcgccccaaccgcaagatgagcggtcagggtcacatggagaccgtgaagagcgccaagcgcctggacgagggcgtgagcgtgctgcgcgt
gccctgacccagctgaagctgaaggacctggagaagatggtgaaccgcgagcgcgagcccaagctgtacgaggccctgaaggcccgcctggagg
cccacaaggacgaccccgccaaggccttcgccgagcccttctacaagtacgacaaggccggcaaccgcacccagcaggtgaaggccgtgcgcgtg
gagcaggtgcagaagaccggcgtgtgggtgcgcaaccacaacggcatcgccgacaacgccaccatggtgcgcgtggacgtgttcgagaagggcga
caagtactacctggtgcccatctacagctggcaggtggccaagggcatcctgcccgaccgcgccgtggtgcagggcaaggacgaggaggactggca
gctgatcgacgacagcttcaacttcaagttcagcctgcaccccaacgacctggtggaggtgatcaccaagaaggcccgcatgttcggctacttcgccag
ctgccaccgcggcaccggcaacatcaacatccgcatccacgacctggaccacaagatcggcaagaacggcatcctggagggcatcggcgtgaagac
cgccctgagcttccagaagtaccagatcgacgagctgggcaaggagatccgccctgccgcctgaagaagcgccctcctgtgcgctaa
```

NM-Cas9-Δ567-654

[SEQ ID NO: 2]

```
atggccgccttcaagcccaaccccatcaactacatcctgggcctggccatcggcatcgccagcgtgggctgggccatggtggagatcgacgaggacg
agaacccatctgcctgatcgacctgggtgtgcgcgtgttcgagcgcgctgaggtgcccaagactggtgacagtctggctatggctcgccggcttgctc
gctctgttcggcgccttactcgccggcgcgctcaccgccttctgcgcgctcgccgcctgctgaagcgcgagggtgtgctgcaggctgccgacttcgacg
agaacggcctgatcaagagcctgcccaacactccttggcagctgcgcgctgccgctctggaccgcaagctgactcctctggagtggagcgccgtgctg
```

-continued ctgcacctgatcaagcaccgcggctacctgagccagcgcaagaacgagggcgagaccgccgacaaggagctgggtgctctgctgaagggcgtggc cgacaacgcccacgccctgcagactggtgacttccgcactcctgctgagctggccctgaacaagttcgagaaggagagcggccacatccgcaaccag cgcggcgactacagccacaccttcagccgcaaggacctgcaggccgagctgatcctgctgttcgagaagcagaaggagttcggcaaccccacgtga gcggcggcctgaaggagggcatcgagaccctgctgatgacccagcgccccgccctgagcggcgacgccgtgcagaagatgctggccactgcacc ttcgagccagccgagcccaaggccgccaagaacacctacaccgccgagcgcttcatctggctgaccaagctgaacaacctgcgcatcctggagcagg gcagcgagcgcccctgaccgacaccgagcgcgccaccctgatggacagccctaccgcaagagcaagctgacctacgcccaggcccgcaagctg ctgggtctggaggacaccgccttcttcaagggcctgcgctacggcaaggacaacgccgaggccagcaccctgatggagatgaaggcctaccacgcc atcagccgcgccctggagaaggagggcctgaaggacaagaagagtcctctgaacctgagccccgagctgcaggacgagatcggcaccgccttcagc ctgttcaagaccgacgaggacatcaccggccgcctgaaggaccgcatccagcccgagatcctggaggccctgctgaagcacatcagcttcgacaagtt cgtgcagatcagcctgaaggccctgcgccgcatcgtgcccctgatggagcagggcaagcgctacgacgaggcctgcgccgagatctacggcgacca ctacggcaagaagaacaccgaggagaagatctacctgcctcctatccccgccgacgagatccgcaaccccgtggtgctgcgcgccctgagccaggcc cgcaaggtgatcaacgcgtggtgcgccgctacggcagccccgcccgcatccacatcgagaccgcccgcgaggtgggcaagagcttcaaggaccg caaggagatcgagaagcgccaggaggagaaccgcaaggaccgcgagaaggccgccgccaagttccgcgagtacttccccaacttcgtgggcgagc ccaagagcaaggacatcctgaagctgcgcctgtacgagcagcagcacggcaagtgcTCCGGCGGCGGTTCGcagaagttcgacgagg acggcttcaaggagcgcaacctgaacgacacccgctacgtgaaccgcttcctgtgccagttcgtggccgaccgcatgcgcctgaccggcaagggcaa gaagcgcgtgttcgccagcaacggccagatcaccaacctgctgcgcggcttctgggggcctgcgcaaggtgcgcgccgagaacgaccgccaccacgc cctggacgccgtggtggtggcctgcagcaccgtggccatgcagcagaagatcacccgcttcgtgcgctacaaggagatgaacgccttcgacggtaaa accatcgacaaggagaccggcgaggtgctgcaccagaagacccacttcccccagccctgggagttcttcgcccaggaggtgatgatccgcgtgttcgg caagcccgacggcaagcccgagttcgaggaggccgacaccccgagaagctgcgcaccctgctggccgagaagctgagcagccgccctgaggcc gtgcacgagtacgtgactcctctgttcgtgagccgcgcccccaaccgcaagatgagcggtcagggtcacatggagaccgtgaagagcgccaagcgcc tggacgagggcgtgagcgtgctgcgcgtgcccctgacccagctgaagctgaaggacctggagaagatggtgaaccgcgagcgcgagcccaagctgt acgaggccctgaaggcccgcctggaggcccacaaggacgaccccgccaaggccttcgccgagcccttctacaagtacgacaaggccggcaaccgc acccagcaggtgaaggccgtgcgcgtggagcaggtgcagaagaccggcgtgtgggtgcgcaaccacaacggcatcgccgacaacgccaccatggt gcgcgtggacgtgttcgagaagggcgacaagtactacctggtgcccatctacagctggcaggtggccaagggcatcctgcccgaccgcgccgtggtg cagggcaaggacgaggaggactggcagctgatcgacgacagcttcaacttcaagttcagcctgcaccccaacgacctggtggaggtgatcaccaaga aggcccgcatgttcggctacttcgccagctgccaccgcggcaccggcaacatcaacatccgcatccacgacctggaccacaagatcggcaagaacgg catcctggagggcatcggcgtgaagaccgccctgagcttccagaagtaccagatcgacgagctgggcaaggagatccgcccctgccgcctgaagaa gcgccctcctgtgcgctaa YFP reporter plasmid

[SEQ ID NO: 3]

agctctcgaaccccagagtcccgctcagaagaactcgtcaagaaggcgatagaaggcgatgcgctgcgaatcgggagcggcgataccgtaaagcac gaggaagcggtcagcccattcgccgccaagctcttcagcaatatcacgggtagccaacgctatgtcctgatagcggtccgccacacccagccggccac agtcgatgaatccagaaaagcggccattttccaccatgatattcggcaagcaggcatcgccatgggtcacgacgagatcctcgccgtcgggcatgcgcg ccttgagcctggcgaacagttcggctggcgcgagcccctgatgctcttcgtccagatcatcctgatcgacaagaccggcttccatccgagtacgtgctcg ctcgatgcgatgtttcgcttggtggtcgaatgggcaggtagccggatcaagcgtatgcagccgccgcattgcatcagccatgatggatactttctcggcag gagcaaggtgagatgacaggagatcctgccccggcacttcgcccaatagcagccagtcccttcccgcttcagtgacaacgtcgagcacagctgcgcaa ggaacgcccgtcgtggccagccacgatagccgcgctgcctcgtcctgcagttcattcagggcaccggacaggtcggtcttgacaaaaagaaccgggc gcccctgcgctgacagccggaacacgcggcatcagagcagccgattgtctgttgtgcccagtcatagccgaatagcctctccacccaagcggccgg agaacctgcgtgcaatccatcttgttcaatcatgcgaaacgatcctcatcctgtctcttgatcagatcttgatccctgcgccatcagatccttggcggcaag aaagccatccagtttactttgcagggcttcccaaccttaccagagggcgccccagctggcaattccgacgtctaagaaaccattattatcatgacattaacc tataaaaataggcgtatcacgaggccctttcgtcttcacctcgaggggacaatgaaaacgttagtcatgcgcgccttgacggctagctcagtcctaggta -continued

```
cagtgctagcttaatgctcgcacatagcagaactttaaaagtattcgccatgttgtagctccctttctcatttcgcagtgctacaatccgccgctatggtcccac
gtagagcatacggaaaaaaagtcaaaagcctccgaccggaggtcggccttacttgctagcagagtttgtagaaacgcaaaaaggccatccgtcagga
tggccttctgcttaatttgatgcctggcagtttatggcgggcgtcctgcccgccaccctccgggccgttgcttcgcaacgttcaaatccgctcccggcggat
ttgtcctactcaggagagcgttcaccgacaaacaacagataaaacgaaaggcccagtctttcgactgagcctttcgttttatttgatgcctggcagttcccta
ctctcgcatggggagaccccacactaccatcggcgctacggcgtttcacttctgagttcggcatggggtcaggtgggaccaccgcgctactgccgccag
gcaaattctgttttatcagaccgcttctgcgttctgatttaatctgtatcaggctgaaaatcttctctcatccgccaaaacagcccgtagaaaagggacgtt
gatcggcacgtaagaggttccacgataaatatctaacaccgtgcgtgttgactattttacctctggcggtgataatggttgcatgtactagaattctttaacttt
aagaaggagatatacatatgaatcccctatggcgaatacttttaaagtctcgtaaaggagaagaacttttcactggagttgtcccaattcttgttgaattagatg
gtgatgttaatgggcacaaattttctgtcagtggagagggtgaaggtgatgcaacatacggaaaacttacccttaaatttatttgcactactggaaaactacct
gttccatggccaacacttgtcactactttcggttatggtctaaaatgctttgctagatacccagatcatatgaaacggcatgactttttcaagagtgccatgccc
gaaggttatgtacaggaaagaactatatttttcaaagatgacgggaactacaagacacgtgctgaagtcaagtttgaaggtgatacccttgttaatagaatc
gagttaaaaggtattgattttaaagaagatggaaacattcttggacacaaattggaatacaactataactcacacaatgtatacatcatggcagacaaacaaa
agaatggaatcaaagttaacttcaaaattagacacaacattgaagatggaagcgttcaactagcagaccattatcaacaaaatactccaattggcgatggc
cctgtccttttaccagacaaccattacctgtcctatcaatctgccctttcgaaagatcccaacgaaaagagagaccacatggtccttcttgagtttgtaacagc
tgctgggattacacatggcatggatgaactatacaaataagcttaaccgaagcgtttgatagttgatatcctttgcctgcggccgcaactagaggcatcaaa
taaaacgaaaggctcagtcgaaagactgggcctttcgttttatctgttgtttgtcggtgaacgctctcctgagtaggacaaatccgccgccctagacctagg
gtacgggttttgctgcccgcaaacgggctgttctggtgttgctagtttgttatcagaatcgcagatccggcttcaggtttgccggctgaaagcgctatttcttc
cagaattgccatgatttttccccacgggaggcgtcactggctcccgtgttgtcggcagcttttgattcgataagcagcatcgcctgtttcaggctgtctatgtg
tgactgttgagctgtaacaagttgtctcaggtgttcaatttcatgttctagttgctttgttttactggtttcacctgttctattaggtgttacatgctgttcat
ctgttacattgtcgatctgttcatggtgaacagctttaaatgcaccaaaaactcgtaaaagctctgatgtatctatcttttttacaccgttttcatctgtgcat
atggacagttttccctttgatatctaacggtgaacagttgttctacttttgtttgttagtcttgatgcttcactgatagatacaagagccataagaacctcaga
tccttccgtatttagccagtatgttctctagtgtggttcgttgttttgcgtgagccatgagaacgaaccattgagatcatgcttactttgcatgtcactcaaa
aattttgcctcaaaactggtgagctgaattttttgcagttaaagcatcgtgtagtgttttttcttagtccgttacgtaggtaggaatctgatgtaatggttgttgg
tattttgtcaccattcatttttatctggttgttctcaagttcggttacgagatccatttgtctatctagttcaacttggaaaatcaacgtatcagtcgggcggc
ctcgcttatcaaccaccaatttcatattgctgtaagtgtttaaatctttacttattggtttcaaaacccattggttaagccttttaaactcatggtagttattt
tcaagcattaacatgaacttaaattcatcaaggctaatctctatatttgccttgtgagttttcttttgtgttagttcttttaataaccactcataaatcctcat
agagtatttgttttcaaaagacttaacatgttccagattatattttatgaatttttttaactggaaaagataaggcaatatctcttcactaaaaactaattcta
attttcgcttgagaacttggcatagtttgtccactggaaaatctcaaagcctttaaccaaaggattcctgatttccacagttctcgtcatcagctctctggtt
gctttagctaatacaccataagcattttccctactgatgttcatcatctgagcgtattggttataagtgaacgataccgtccgttctttccttgtagggttttc
aatcgtggggttgagtagtgccacacagcataaaattagcttggtttcatgctccgttaagtcatagcgactaatcgctagttcatttgctttgaaaacaacta
attcagacatacatctcaattggtctaggtgattttaatcactataccaattgagatgggctagtcaatgataattactagtccttttcctttgagttgtgggt
atctgtaaattctgctagacctttgctggaaaacttgtaaattctgctagaccctctgtaaattccgctagacctttgtgtgttttttttgtttatattcaagt
ggttataatttatagaataaagaaagaataaaaaagataaaagaatagatcccagccctgtgtataactcactactttagtcagttccgcagtattacaaaa
ggatgtcgcaaacgctgtttgctcctctacaaaacagaccttaaaacccaaaaggcttaagtagcaccctcgcaagctcgggcaaatcgctgaatattccttt
gtctccgaccatcaggcacctgagtcgctgtcttttcgtgacattcagttcgctgcgctcacggctctggcagtgaatgggggtaaatggcactacaggcgcc
ttttatggattcatgcaaggaaactacccataatacaagaaaagcccgtcacgggcttctcagggcgttttatggcgggtctgctatgtggtgctatctgactU
ttgctgttcagcagttcctgccctctgattttccagtctgaccacttcggattatcccgtgacaggtcattcagactggctaatgcacccagtaaggcagcggt
atcatcaacaggcttacccgtcttactgtccctagtgcttggattctcaccaataaaaaacgcccggcggcaaccgagcgttctgaacaaatccagatggagtt
ctgaggtcattactggatctatcaacaggagtccaagcg.
```

According to the methods described herein, several deletions within NM-Cas9 have been identified, the largest NM-Cas9-Δ255-449 removes 595 basepairs and shows only a 16% decrease in activity as measured by the reporter assay. According to certain aspects, mutant Cas9 proteins are provided which have 1000 fewer base pairs or 900 fewer base pairs compared to the wild type Cas9, such as NM-Cas9 and retain near wild-type levels of activity.

Example II

Targeting Cas9 Nuclease Domains for Deletion

Along with targeting regions of low sequence conservation or between sequence conservation edges in the case where a nickase or nuclease null allele of Cas9 is desired, one can target the Cas9 nuclease domains along with their surrounding nucleotides for deletion. Utilizing such an approach, a functional NM-Cas9 allele lacking the HNH motif and surrounding nucleotides NM-Cas9-Δ567-654 was made which retained near wild-type ability to bind DNA as determined by the YFP reporter assay.

Example III

Methods to Construct a Non-biased NM-Cas9 Deletion Library

Aside from taking a targeted approach to generating Cas9 deletions, aspects of the present disclosure include a high-throughput approach for random deletion creation and screening of functional mutants. According to an exemplary method, plasmid DNA containing the desired Cas9 allele can be sheared using a promiscuous nuclease, sonication, repeatedly pipetting the sample, or other chemical, enzymatic or environmental means. Once fragmented, the plasmid DNA can be treated with exonucleases to remove nucleotides from the Cas9 gene. After exonuclease treatment, fragmented ends are made blunt ended with enzymes such as Mung Bean nuclease or Klenow polymerase and ligated together to regenerate a Cas9 plasmid containing a random deletion. To insert an exogenous domain such as a linker or effector motif within the deleted portion of Cas9, such domains can be ligated to the blunt ended fragmented DNA, and subsequent circularization of the plasmid will produce a Cas9 coding sequence where the exogenous domain has been inserted within the deleted portion of Cas9. The library of circularized molecules will then be transformed into *E. coli* and plasmid DNA will be extracted. At this point, the library can be transformed into cells containing a reporter assay for Cas9 activity and members of the library that maintain functional activity can be identified. Alternatively, to reduce the size of the library to be screened, the coding sequence for Cas9 from the newly generated library can be isolated via digestion or PCR and the fragments can be size-selected to be shorter than the initial wild-type Cas9 gene. These smaller members can then be ligated back into the starting vector and transformed into cells containing the reporter of Cas9 activity.

Aside from plasmid shearing, a library of oligonucleotides can be generated that have 3' homology to the Cas9 gene but contain 5' homology to each other, where the 3' end of each oligonucleotide binds to a different stretch of around 30 basepairs within Cas9. These oligonucleotides cover both the sense and anti-sense strands of the Cas9 coding sequence. PCR can then be performed with these oligonucleotides to generate a series of Cas9 fragments with each product from a given sense PCR reaction having complementarity to all other anti-sense PCR products and vice-versa. These fragments can then be annealed together using methods such as Gibson assembly or overlap extension PCR followed by ligation into a vector backbone and transformed into cells, generating a library of Cas9 variants with random stretches of the Cas9 gene removed. For longer linkers or to insert an effector domain within the deleted regions, the oligonucleotides on their 5' ends should contain complementarity towards the longer linker or effector domain and this domain should then be included in the Gibson assembly reaction or during overlap extension PCR. Once a library has been generated, functional variants can be identified using a reporter assay such as the YFP reporter system described herein.

Example IV

Vector Construction

Cas9 nuclease null plasmids were ST1 (Addgene #48659) or were constructed from plasmids NM and TD (Addgene #48646 and 48648, respectively) by introducing the following point mutations (NM: D16A D587A H588A N611A and TD: D13A D878A H879A N902A). Cas9 deletions were generated using Gibson assembly. Internal deletions when made were joined by a 5 amino acid Ser-Gly-Gly-Gly-Ser linker, except for NM Δ566-620 which lacks a linker between joined fragments. The N-terminal domain exchange fused residues 1-117 of ST1 onto residues 118-1082 of NM. The C-terminal domain exchange fused residues 1-727 of NM onto residues 743-1121 of ST1.

Example V

Bacterial Reporter Constructs

Reporter constructs used for analysis of the deletion mutants are similar to those previously published except they combine the spacer element and YFP reporter into a single SC101-kanR plasmid backbone. Reporter constructs for domain-exchange analysis are identical to those used previously. See Esvelt, K. M. et al. Orthogonal Cas9 proteins for RNA-guided gene regulation and editing. *Nature methods* 10, 1116-1121, doi:10.1038/nmeth.2681 (2013) hereby incorporated by reference in its entirety.

Example VI

Mammalian Reporter Constructs

M-ST1n-VP64 construct, ST1 guideRNA plasmid and ST1 specific mammalian transcriptional reporter were previously published in Esvelt, K. M. et al. Orthogonal Cas9 proteins for RNA-guided gene regulation and editing. *Nature methods* 10, 1116-1121, doi:10.1038/nmeth.2681 (2013) (Addgene #48675, 48672 and 48678, respectively). Deletion mutants were made as in the bacterial constructs.

Example VII

Repression Assays

Cas9 repression assays were performed by co-transforming NEB 10-beta cells (New England BioLabs) with the appropriate spacer/reporter construct and Cas9 vector to be investigated. Colonies from transformations were picked and grown at 37° C. with continuous shaking in 96 well plates. Plates were read the following day using a Synergy Neo microplate reader (BioTek), measuring fluorescence at 495-528 nm and absorbance at 600 nm. For swap experiments two different previously published spacer/protospacer combinations (A and B) (see Esvelt, K. M. et al. Orthogonal Cas9 proteins for RNA-guided gene regulation and editing. *Nature methods* 10, 1116-1121, doi:10.1038/nmeth.2681 (2013)) were tested. For all other experiments, only spacer/protospacer combination B was examined.

Example VIII

Cell Culture and Transfections

HEK 293T cells were maintained in Dulbecco's modified Eagle's medium (Invitrogen) with high glucose supplemented with 10% FBS (Invitrogen) and penicillin/streptomycin (Invitrogen). Cells were maintained at 37° C. and 5% $CO_2$ in a humidified incubator. Cells were transfected in 24 well plates seeded with 50,000 cells per well. 400 ng of Cas9 activator, 100 ng of gRNA and 60 ng of reporter plasmid were delivered to each well using 2.5 ul of Lipofectamine 2000. Cells were grown an additional 36-48 hours before being assays using immunofluorescence or FACS.

Example IX

Multiple Sequence Alignments and Edge Filter

Multiple sequence alignments were made by re-aligning Cas9 sequences in the PFAM database (PF13395, 798 sequences) in MUSCLE, and conditioning the alignment for diversity and full-length sequences using a MATLAB script. This method described in more detail below yielded 217 sequences.

Figure 2A:
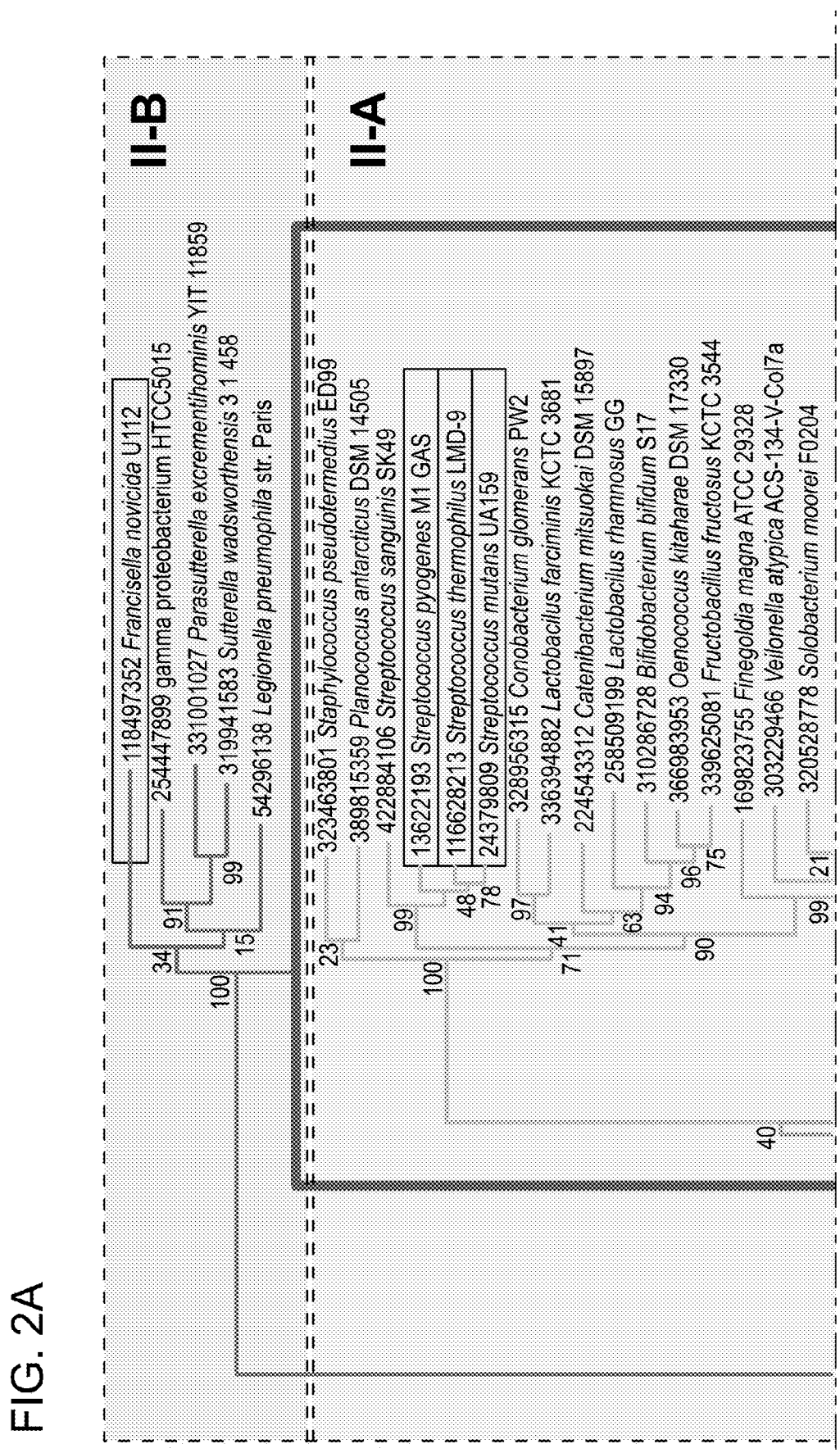
FIGS. 2A-2D are a phylogenetic tree as described in Fonfara I, et al., (2014) Phylogeny of Cas9 determines functional exchangeability of dual-RNA and Cas9 among orthologous type II CRISPR-Cas systems, Nucleic Acids Res. 42, 2577-90 hereby incorporated by reference in its entirety. Marked in red are sequences used as an initial seed for the PFAM realignment.
Figure 2B:
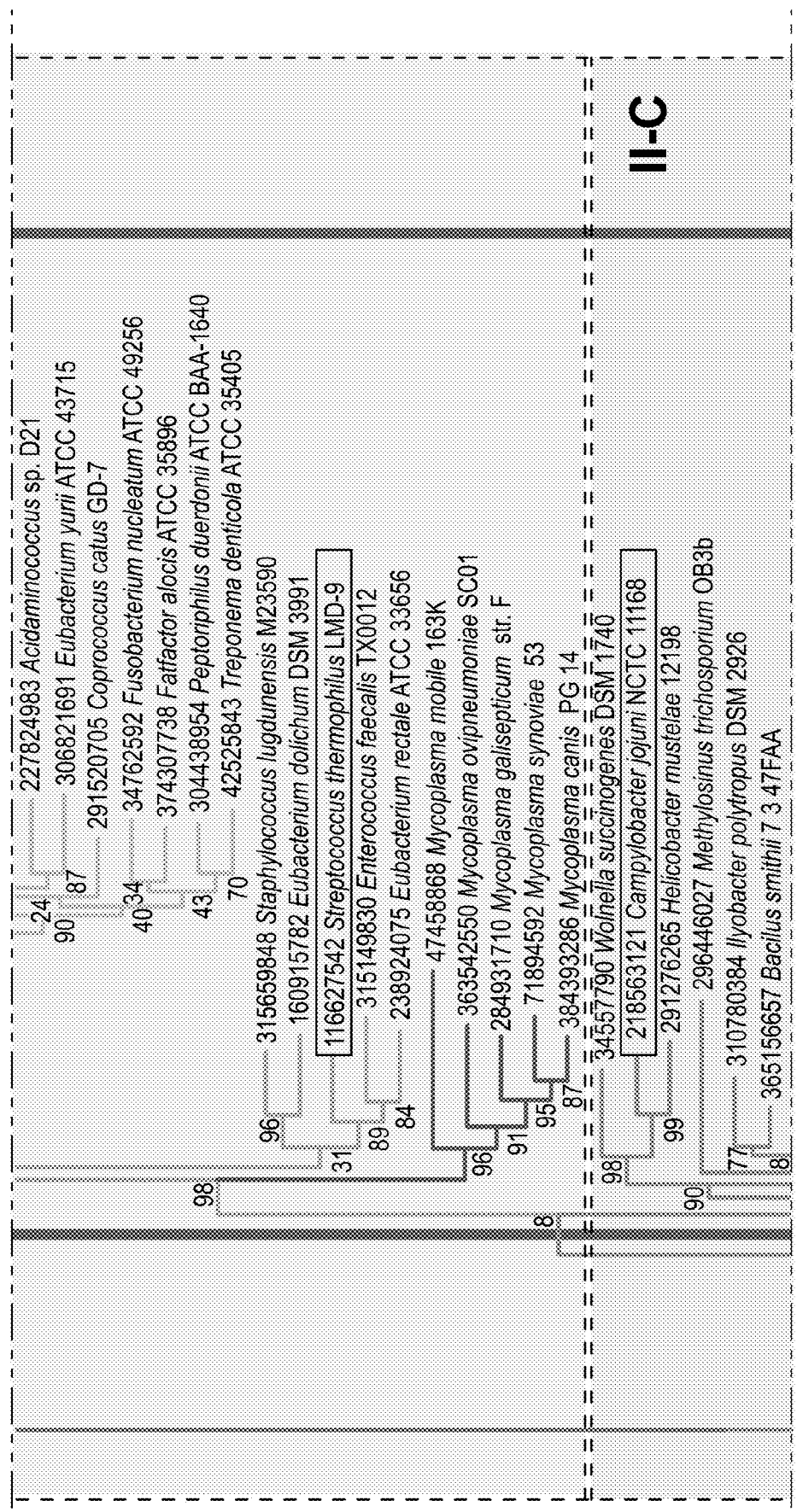
Figure 2C:
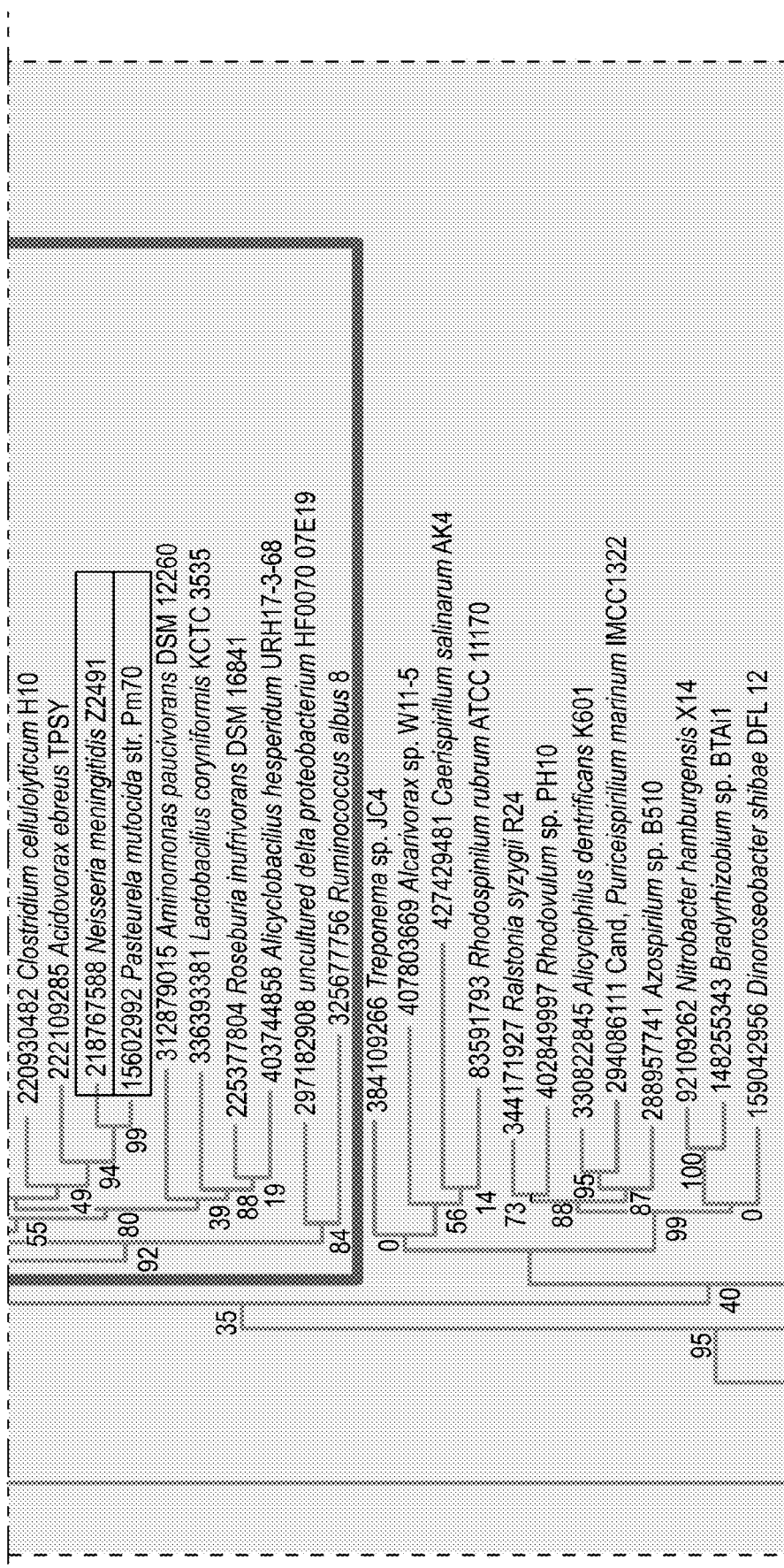
Figure 2D:
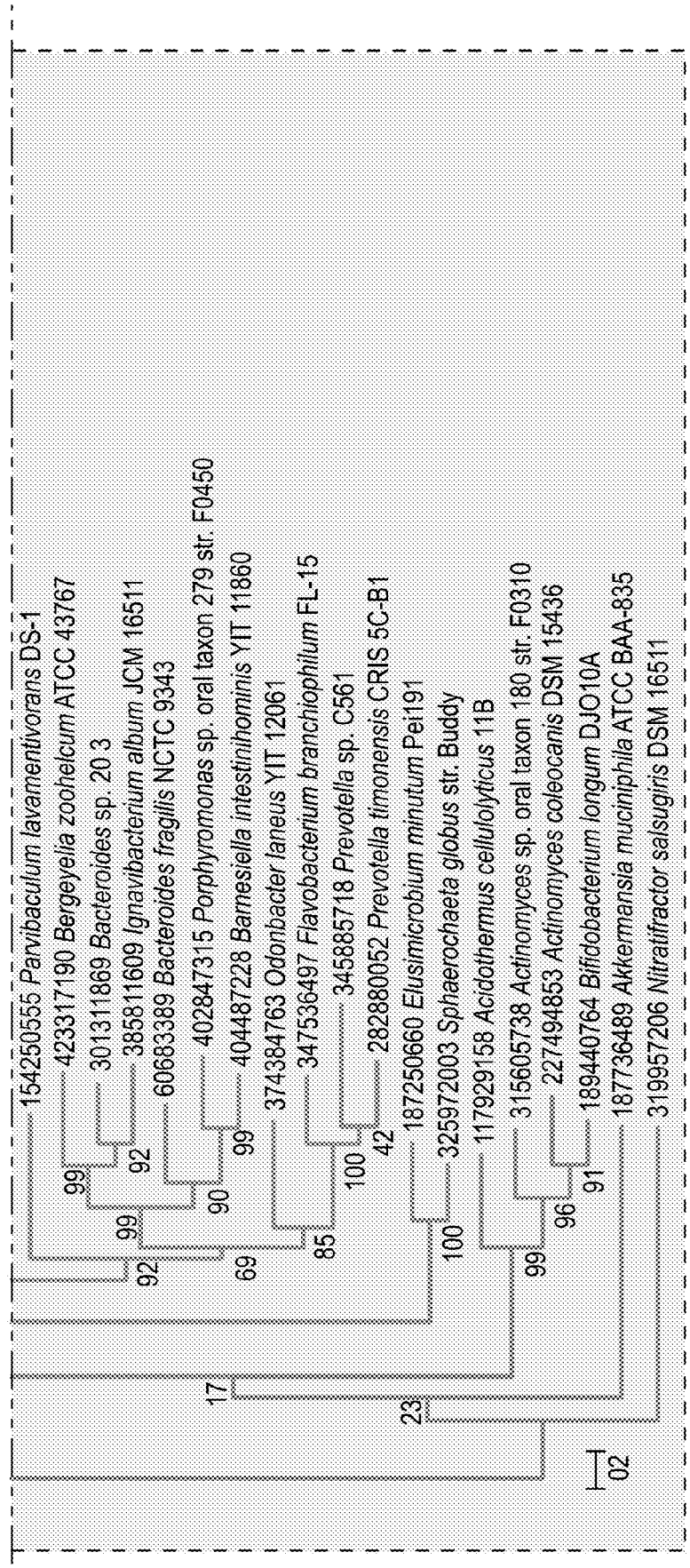

In order to arrive at the final re-alignment of the Cas9 sequences in the PFAM database (PF13395, 798 sequences), the following steps (all program code in MATLAB) were carried out. The alignment from Fonfara I, et al., (2014) Phylogeny of Cas9 determines functional exchangeability of dual-RNA and Cas9 among orthologous type II CRISPR-Cas systems, *Nucleic Acids Res.* 42, 2577-90 was obtained and only sequences from group IIA and IIC were included, and from the latter only up to the branch that separates IIA and IIC (marked in red box in FIGS. 2A-2C) which included 49 total sequences.

The sequences were then split into two groups, one with and one without the large insertion at approximately position 150 (which distinguishes e.g. between NM-Cas9 and ST-Cas9 on one hand and SP-Cas9 and TD-Cas9 on the other). These groups are separately aligned using MUSCLE (see Edgar, R C (2004) MUSCLE: multiple sequence alignment with high accuracy and high throughput, *Nucleic Acids Res* 32, 1792-97, re-aligned using a windowed approach (because of the length of the sequences), and then profile-profile aligned back into one seed alignment.

The sequences in PF13395 are realigned with MUSCLE and using the seed alignment. All alignments using a seed are performed by aligning each of the target sequences one-by-one to the seed. This alignment is used to determine the top-hit identity between seed and target sequences, which are re-ordered according to decreasing top-hit identity. The target sequences are then again aligned to the seed one-by-one, now in order of decreasing identity. This two-step approach is taken to ensure the robustness of the alignment. Also these sequences are split depending on whether they contain the insertion or not, and the two separate groups are re-aligned with the seed as a profile. Short sequences and sequences with large truncations are removed manually. Sequences with higher than 90% pair-wise similarity are removed.

The resulting two alignments are profile-profile aligned to each other which resulted in the 217 total sequences. The resulting alignments are truncated to the positions of the Cas9 ortholog of interest.

Sequence conservation was calculated as the relative entropy with respect to the background frequency of amino acids averaged over all genes in *Escherichia coli* O157. Domain boundary detection was performed by applying a Difference of Gaussians (DoG) edge filter (see Marr, D. & Hildreth, E. Theory of edge detection. *Proceedings of the Royal Society of London. Series B, Containing papers of a Biological character. Royal Society* 207, 187-217 (1980) hereby incorporated by reference in its entirety) to the resulting conservation profile, averaging over multiple length scales to achieve robustness to choice of parameters and detection at various length scales.

Figure 3:
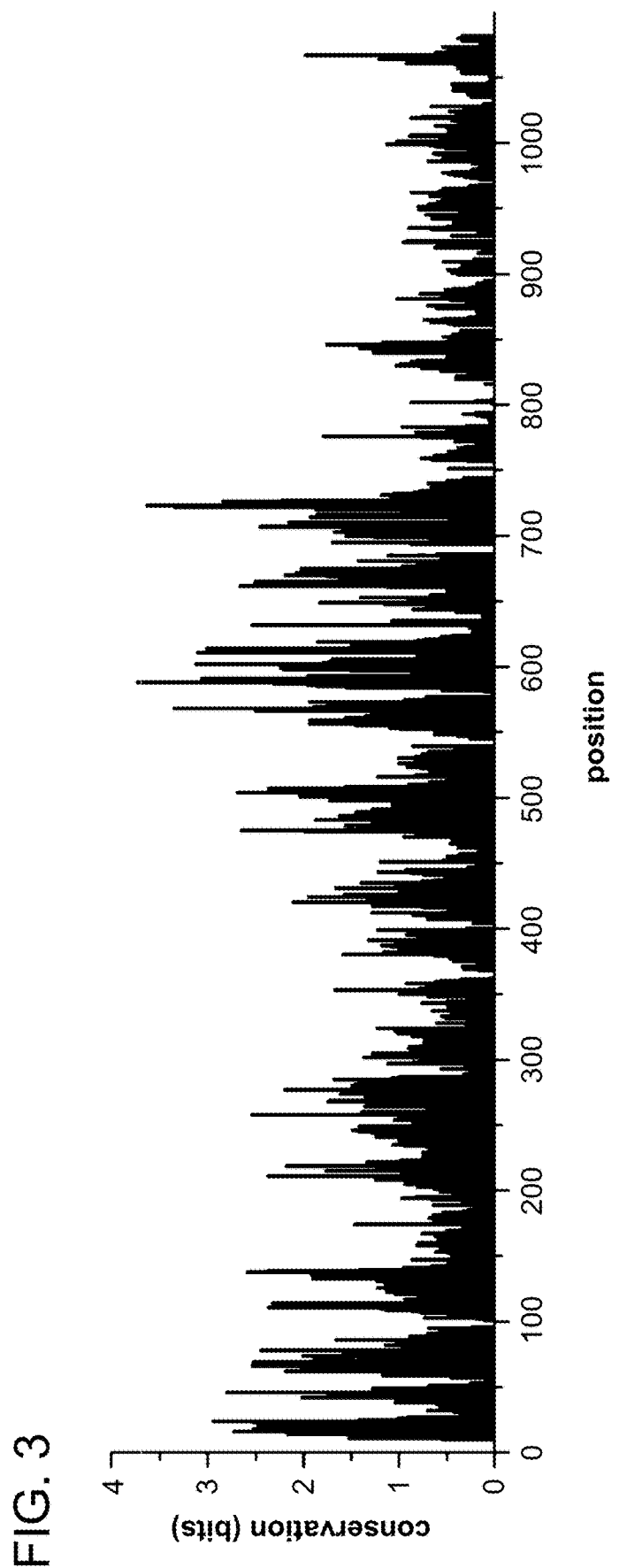
FIG. 3 is a conservation profile of Cas9 alignment after truncation to positions of NM-Cas9.

In particular, the conservation of the alignment was calculated, being the relative entropy (see Cover, T M and Thomas, J T (2006) Elements of Information Theory; 2nd edition, Wiley-Interscience) of amino acid frequencies with respect to the average frequencies for all genes in *Escherichia coli* O157:

$$D_i = \sum_{a=1}^{20} p_i^a \log \frac{p_i^a}{q^a}$$

where $p_i^a$ is the frequency of amino acid a at position i, and $q^a$ is the average frequency of amino acid a. Summation is over all 20 amino acids. The log is base 2 and the entropy is given in bits. Average frequencies $q^a$ are as follows: {A C D E F G H I K L M N P Q R S T V W Y}=0.094 0.012 0.052 0.058 0.038 0.073 0.022 0.059 0.045 0.104 0.027 0.041 0.044 0.044 0.057 0.060 0.055 0.070 0.015 0.029. The Cas9 alignment yields the conservation profile in FIG. 3, after truncation to positions of NM-Cas9.

Figure 4:
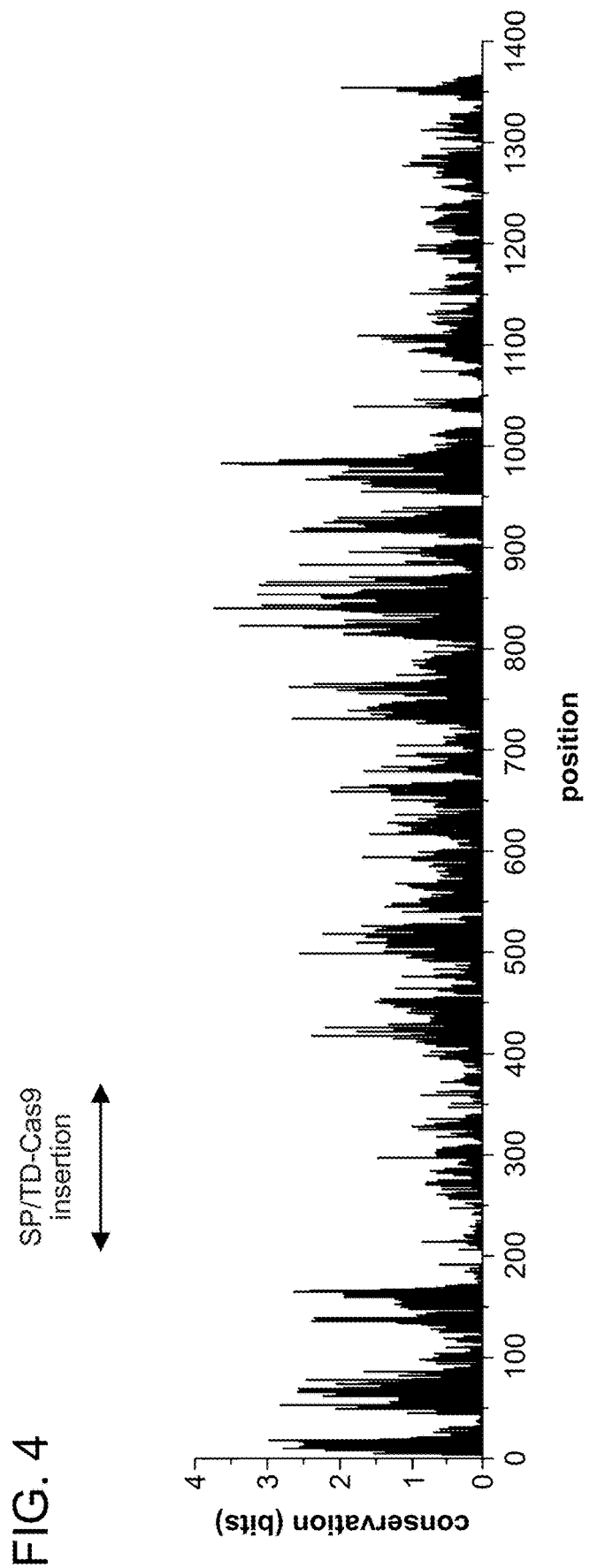
FIG. 4 is a conservation profile truncated to positions in SP-Cas9.

The conservation profile is plotted truncated to positions in SP-Cas9 (which is an example of the larger Cas9-proteins from the type IIA subfamily) Similar features are observed at the N-terminal approximately until position NM145 (SP170) and then again after position NM200(SP400), which is the large insertion described above. See FIG. 4.

Potential domain boundaries were identified by applying a multi-scale edge filter to the conservation profile. This filter calculates the difference of Gaussians (DoG) (see Man, D and Hildreth, E (1980) Theory of Edge Detection, *Proc R Soc Lond B Biol Sci* 207, 187-217 hereby incorporated by reference in its entirety) for a range of scales and sums the resulting graphs. The extrema of this curve are interpreted as the boundaries between lowly and highly conserved regions in the protein. Domains may exhibit different levels of conservation due to their potentially different functional importance leading to differential rates of evolutionary divergence. Differential conservation may be characteristic of a multi-domain protein that is the result of domain insertion over evolutionary timescales. The values of the extrema are used to rank-order the boundaries in terms of importance.

For the Cas9 alignment, restricted to NM positions, the following boundaries or conservation edges or edge amino acids were identified using the methods described herein:

| Rank | Position | Abs Val of Extremum |
|------|----------|---------------------|
| 1    | 736      | 0.0225              |
| 2    | 620      | 0.0148              |
| 3    | 554      | 0.0148              |
| 4    | 472      | 0.0144              |
| 5    | 288      | 0.0136              |
| 6    | 144      | 0.0131              |
| 7    | 87       | 0.0106              |
| 8    | 661      | 0.0101              |
| 9    | 825      | 0.0100              |
| 10   | 205      | 0.0099              |
| 11   | 512      | 0.0092              |
| 12   | 414      | 0.0092              |
| 13   | 108      | 0.0092              |
| 14   | 853      | 0.0067              |
| 15   | 438      | 0.0050              |
| 16   | 936      | 0.0041              |
| 17   | 1011     | 0.0038              |

Example X

Computational Analysis of Cas9 Family Members

In order to identify regions within the multi-domain Cas9 protein that may be amenable to deletion, a bioinformatics approach was used to identify potential boundaries between domains. Using a well-curated seed alignment, full-length Cas9 sequences from PFAM (PF13395) were realigned and sequences with high pairwise identity were removed as desceibed above. The first-order sequence conservation was calculated as the relative entropy (see Cover, T. M., Thomas, J. T. Elements of Information Theory, 2nd edition. (Wiley-Interscience, 2006)) of observed amino acid frequencies with respect to the average frequencies across all genes in Escherichia coli. As domains in a multi-domain protein can be expected to exhibit varying levels of sequence conservation, applying a multi-scale edge filter to the conservation profile may be sued to identify locations of the domain boundaries.

Figure 5A:
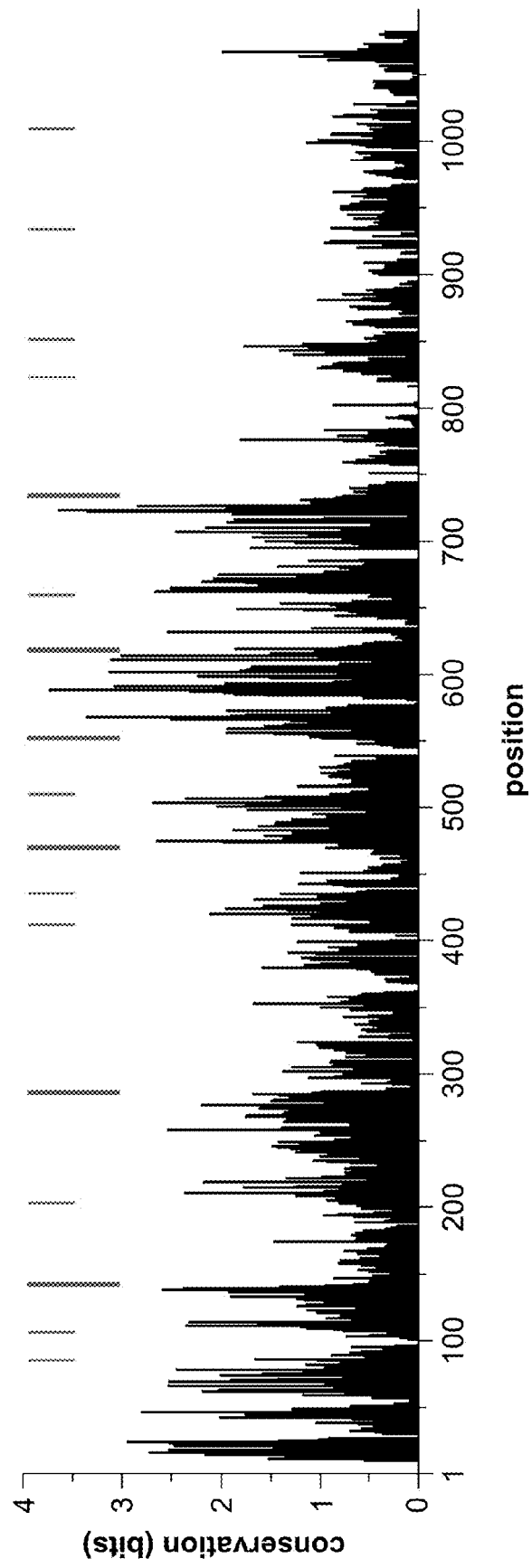
FIG. 5A is a plot of first-order amino acid conservation within Cas9 proteins. Relative entropies are calculated with respect to the average amino acid frequency across all genes in Escherichia coli. Vertical lines above plot represent boundaries determined by the alignment-based boundary detection algorithm, with bold lines representing the six most significant boundaries detected.
Figure 5B:
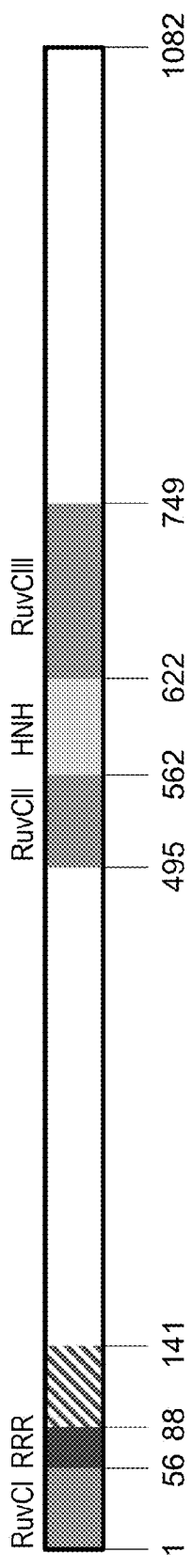
FIG. 5B shows domain assignments based on Fonfara, I. et al. Phylogeny of Cas9 determines functional exchangeability of dual-RNA and Cas9 among orthologous type II CRISPR-Cas systems. Nucleic acids research 42, 2577-2590, doi:10.1093/nar/gkt1074 (2014) hereby incorporated by reference in its entirety. RuvCI-III are the parts folding into the RuvC nuclease domain HNH is the HNH nuclease domain. RRR is the arginine-rich alpha-helical region. Cross-hatched is the extension of this region based on the arginine-rich stretch around position 140.

Edge detection on the conservation profile was performed with a difference of Gaussians (DoG) band-pass filter that is sensitive to a narrow range of spatial frequencies. See Marr, D. & Hildreth, E. Theory of edge detection. Proceedings of the Royal Society of London. Series B, Containing papers of a Biological character. Royal Society 207, 187-217 (1980). In order to allow detection at various length scales and to make the filter insensitive to a particular choice of parameters, an averaging over multiple scales (5-50 amino acids) was carried out. The band-pass filter was then applied to the conservation profile for the Cas9 alignment. The identified potential boundary positions for NM-Cas9 are shown in FIG. 5A, with the top 6 ranking boundaries in bold longer red lines. As can be seen, the filter correctly identifies the known HNH and RuvC domain arrangements that were assigned previously in Sapranauskas, R. et al. The Streptococcus thermophilus CRISPR/Cas system provides immunity in Escherichia coli. Nucleic acids research 39, 9275-9282, doi:10.1093/nar/gkr606 (2011) and Fonfara, I. et al. Phylogeny of Cas9 determines functional exchangeability of dual-RNA and Cas9 among orthologous type II CRISPR-Cas systems. Nucleic acids research 42, 2577-2590, doi:10.1093/nar/gkt1074 (2014) each of which are incorporated by reference in its entirety (see FIG. 5B), starting upstream of position 500 and ranging until position 750. Boundaries between the domains, at around positions 560 and 620, are also correctly predicted. Also the boundary of the first arginine-rich alpha-helix at position 88 is predicted. One of the top-ranking boundaries on the N-terminal side of the protein, at position 144, was not identified as a domain boundary previously in Fonfara, I. et al. Phylogeny of Cas9 determines functional exchangeability of dual-RNA and Cas9 among orthologous type II CRISPR-Cas systems. Nucleic acids research 42, 2577-2590, doi:10.1093/nar/gkt1074 (2014), but represents a better delineation of the Arg-rich alpha-helical region, now including a second conserved arginine-rich helix.

Example XI

Truncation and Deletion Analysis of Cas9

Figures 6A, 6B, 6C:
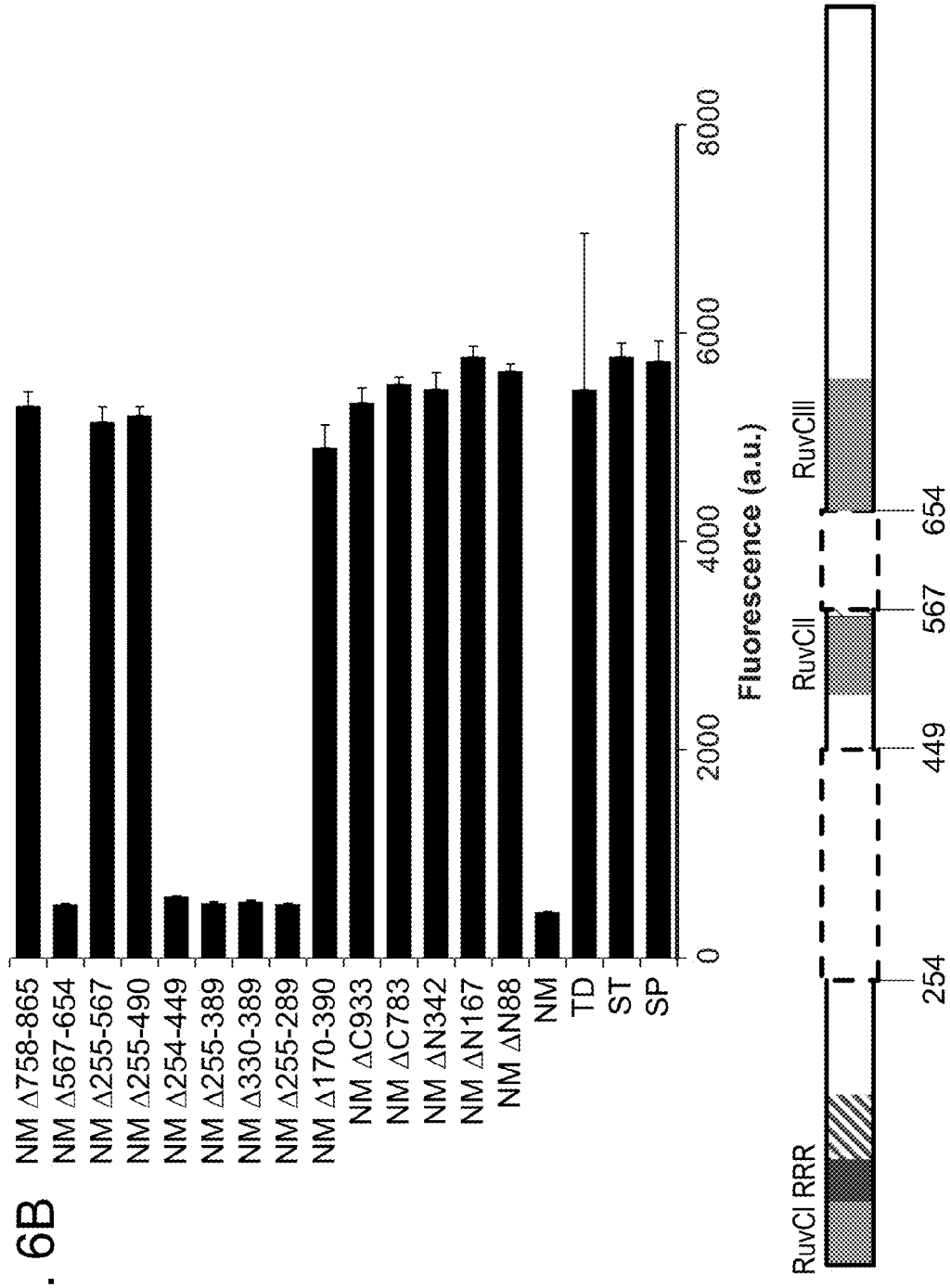
FIG. 6A is a schematic depicting design of NM Cas9 transcriptional reporter. The location of the protospacer and NM specific PAM are noted.
FIG. 6B is a graph of NM Cas9 transcriptional repression assay data with various nuclease null NM mutants tested in E. coli. Data represent mean±standard deviation (n=4).
FIG. 6C is a schematic depicting NM Cas9 domain structure. White boxes with dashed outlines give the extent of the largest excised regions from NM mutants that cause minimal alteration in DNA binding activity.
Figure 7:
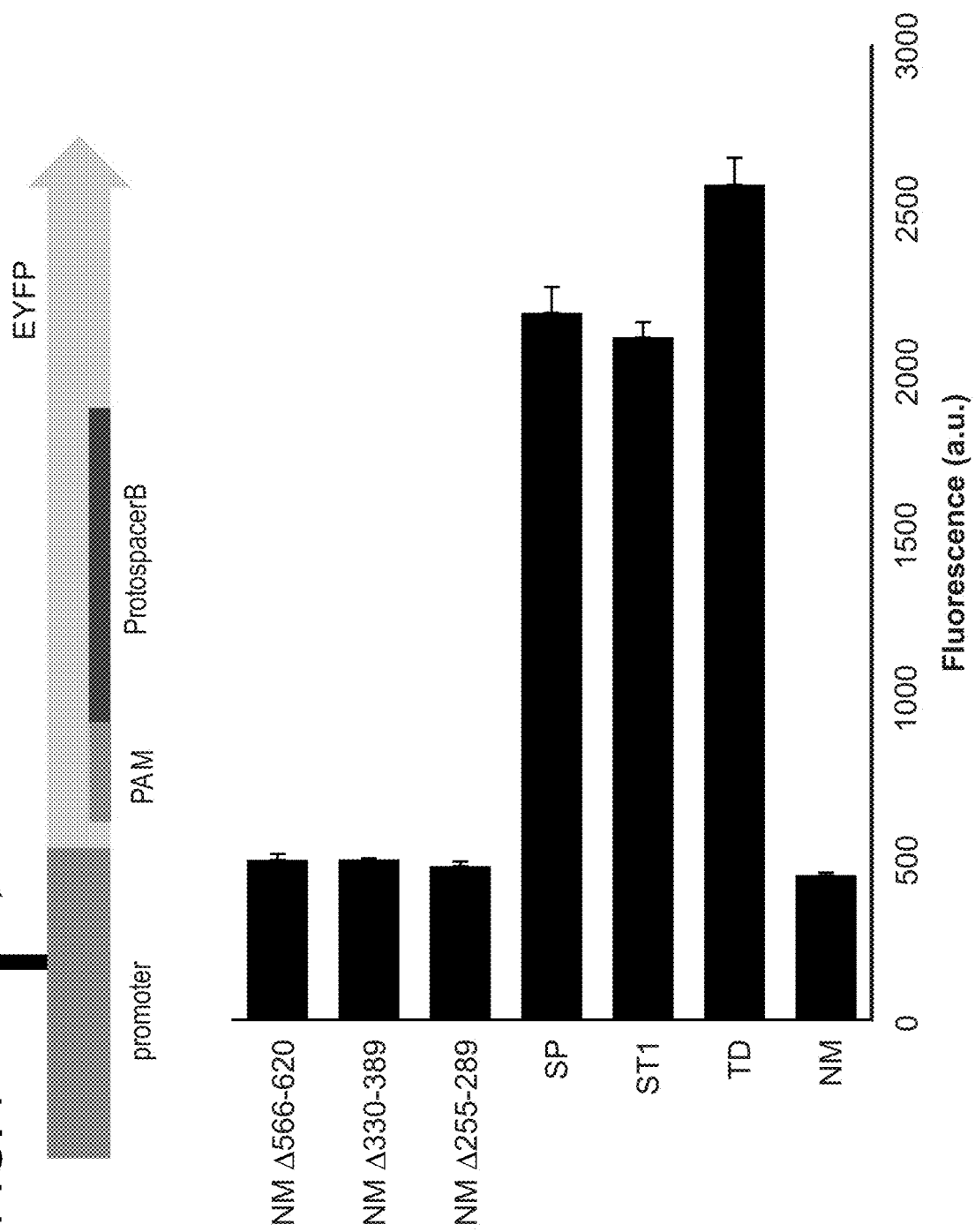
FIG. 7 is directed to NM Cas9 deletion analysis and depicts design of NM Cas9 transcriptional reporter. The location of the protospacer and NM specific PAM are noted. NM Cas9 transcriptional repression assay with various nuclease null NM mutants were tested in E. coli. Data represent mean±standard deviation (n=5).

To explore functional and potentially non-functional domains within Cas9 experimentally N and C-terminal truncations were generated, along with a set of modest internal deletions based upon the domain detection analysis described herein. The effects of the deletions were analyzed using a transcriptional repressor assay in Escherichia coli, in which a functional nuclease-null Cas9 protein will bind to the 5' end of a YFP reporter, thereby lowering its expression level (see FIG. 6A). See Qi, L. S. et al. Repurposing CRISPR as an RNA-guided platform for sequence-specific control of gene expression. Cell 152, 1173-1183, doi:10.1016/j.cell.2013.02.022 (2013); Esvelt, K. M. et al. Orthogonal Cas9 proteins for RNA-guided gene regulation and editing. Nature methods 10, 1116-1121, doi:10.1038/nmeth.2681 (2013) and Bikard, D. et al. Programmable repression and activation of bacterial gene expression using an engineered CRISPR-Cas system. Nucleic acids research 41, 7429-7437, doi:10.1093/nar/gkt520 (2013) each of which are hereby incorporated by reference in its entirety. None of the N- or C-terminal truncations were able to repress the reporter, while two internal deletions, NMΔ255-289 and NMΔ330-389, downstream and upstream of the boundary at position 288, along with an NMΔ566-620 deletion showed near wild-type levels of repression (FIG. 6B and FIG. 7). Several rounds of additional analysis were performed in which the deletions were iteratively expanded and the ability to repress the reporter (FIG. 6B) was assayed. Two large non-overlapping regions 254-449 and 567-654 (comprising 18% and 8% of the total length of the protein, respectively) were identified that could be removed with negligible loss in NM activity (FIG. 6C). As seen from the alignment, NM positions 254-449 represent a stretch of relatively low conservation, in a region of the protein that is specific to Cas9 proteins. Positions 567 to 654 represent the HNH domain, a domain known to be critical in Cas9 DNA catalysis but was found to be dispensable for DNA binding.

Figure 8A:
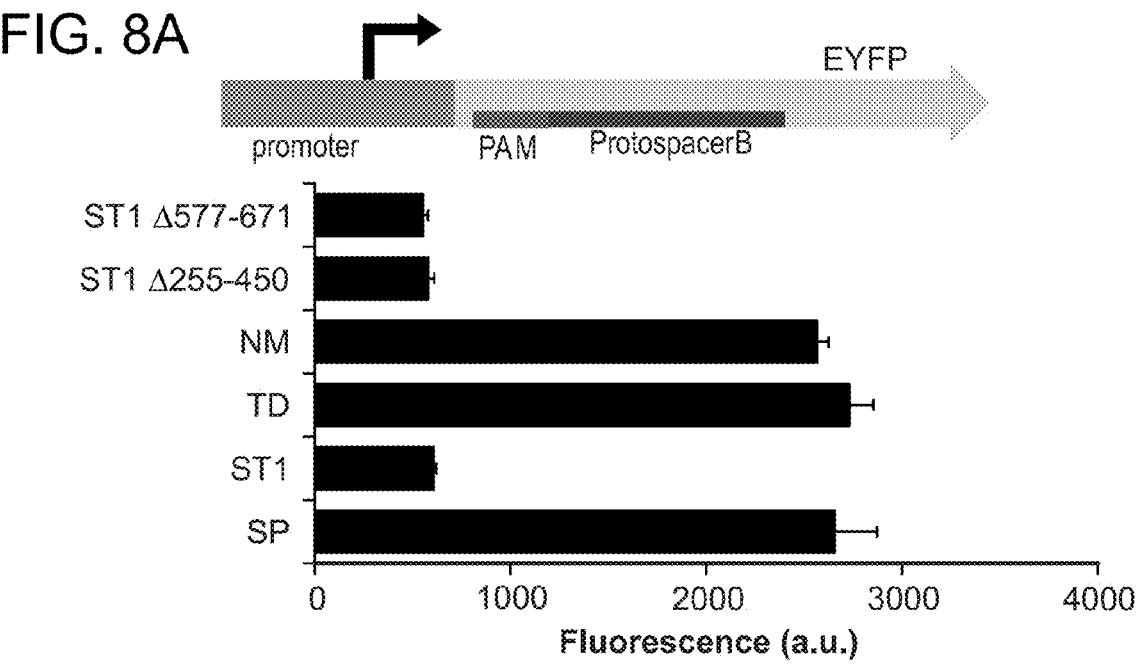
FIG. 8A depicts ST1 Cas9 deletion analysis and functional validation in E. coli and human cells and in particular, design of ST1 Cas9 transcriptional reporter. The location of the protospacer and ST1 specific PAM are noted. ST1 Cas9 transcriptional repressor assay with ST1 nuclease-null deletion mutants tested in E. coli. Data represent mean±standard deviation (n=4).
Figure 9:
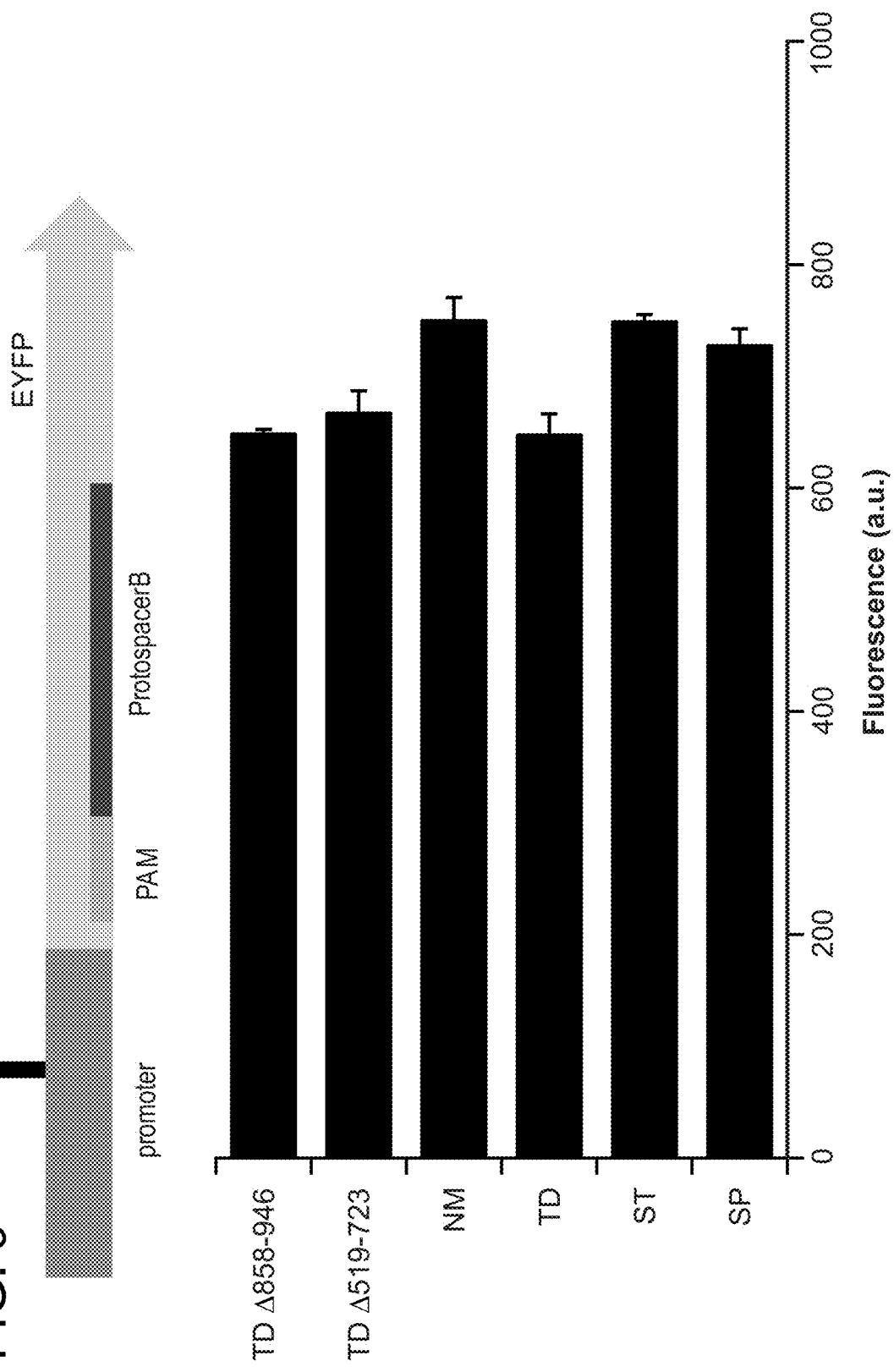
FIG. 9 is directed to TD Cas9 deletion analysis and functional validation in E. coli. TD nuclease-null deletion mutants were tested using a transcriptional repressor assay. Data represent mean±standard deviation (n=4).
Figure 11A:
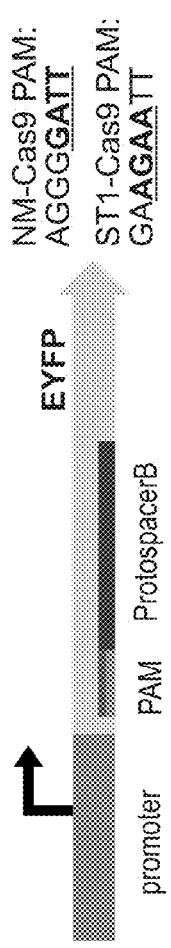
FIG. 11A is directed to NM-ST1 domain swap analysis as determined by a transcriptional repression assay, and in particular, design of ST1 transcriptional reporter with the sequence of the ST1 specific PAM illustrated.
Figure 11B:
FIG. 11B is a schematic outline of NM and ST1 Cas9 with the location of the amino acid swap points noted.
Figure 11D:
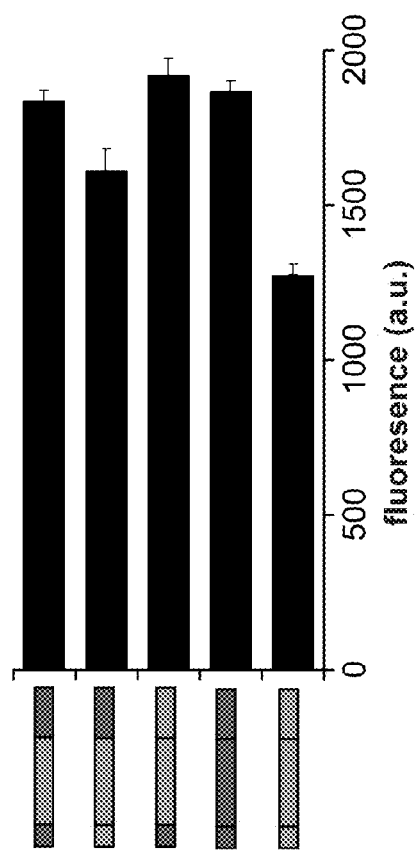
FIG. 11C-11D are graphs of fluorescence for NM-ST1 nuclease null domain exchange mutants expressed in conjunction with guide RNAs particular to NM (FIG. 11D) or ST1 Cas9 (FIG. 11C) along with reporters with PAM sequences specific to ST1 Cas9 (FIGS. 11C and 11D). Data represent mean±standard deviation (n=4).
Figure 11C:
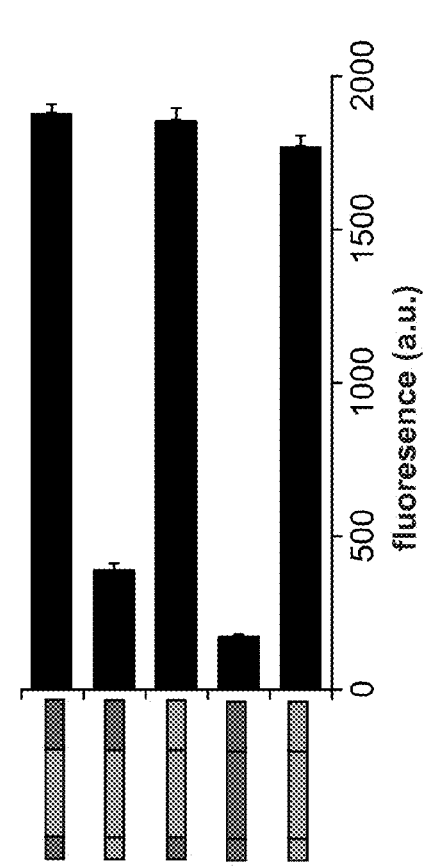

To corroborate that the regions removed from NM-Cas9 were not unique to NM but represent general regions that can be removed from other Cas9 family members, the corresponding deletions were generated within nuclease null-variants of Streptococcus thermophilus Cas9 (ST1) and Treponema denticola Cas9 (TD, GI: 42525843) and their function with the transcriptional repression assay was measured (FIG. 8A and FIG. 9). Corresponding deletion mutants in both ST1 and TD showed activities similar to their wild-type counterparts, suggesting that the removed regions are dispensable for Cas9 DNA binding throughout the Cas9 phylogeny, even among more distant members within the type II-A subfamily such as TD.

Figure 8B:
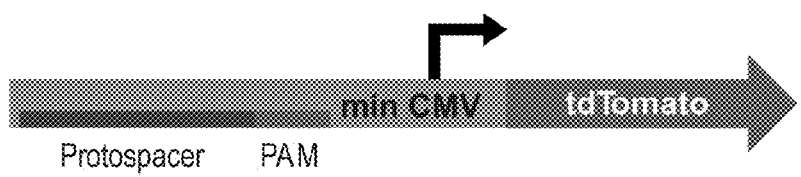
FIG. 8B is a schematic depicting reporter construct for testing ST1 activation which contains a minimal CMV promoter (min CMV) upstream of a tdTomato reporter. ST1 nuclease null Cas9-VP64 fusion proteins binding upstream of the minimal CMV promoter lead to transcriptional activation and fluorescence within human cells.
Figure 8C:
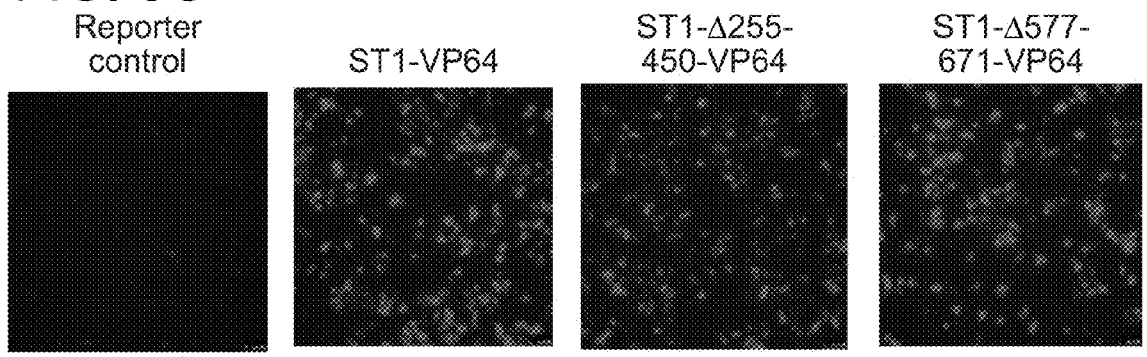
FIG. 8C are images of cells transfected with ST1 activators including deletion mutants were transfected along with sgRNAs and the tdTomato reporter and were visualized by fluorescence microscopy.
Figure 8D:
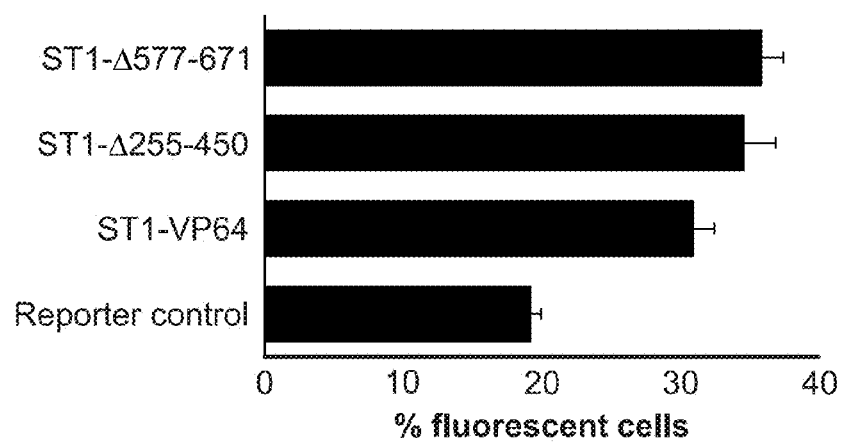
FIG. 8D is a graph showing quantification of ST1 activation from panel C by flow cytometry. Data represent mean±standard deviation (n=3).

The activity of the two largest functional deletions described herein were tested within ST1-Cas9 using a transcriptional activator assay (FIG. 8B). In agreement with the analysis within E. coli, both ST1 deletion mutants retained activity comparable to the wild-type protein when fused to the VP64 activation domain and targeted to a fluorescent reporter in human cells (FIG. 8C-8D). The larger of the two deletion mutants Δ255-450 (ST1 numbering) generates a Cas9 gene that is 2,793 base pairs in size.

Example XII

Cas9 Domain Exchange

The Cas9 N- and C-terminal domains may play critical roles in crRNA:tracrRNA binding and/or PAM selectivity. To analyze activity, a series of domain exchange mutants between NM and ST1 were made, replacing the N and/or C terminus of NM with the homologous region from ST1. The chimeric proteins were then tested using the transcriptional reporter assay described herein altering the guideRNA and/or Cas9 specific PAM within the reporter to determine the influence of the domain exchanges on protein specificity (FIG. 10A). The exact positions for the domain swaps were determined based on domain boundary analysis: positions were selected that were as close as possible to the most significant N- and C-terminal boundaries identified (FIG. 5A), that were at the same time nearly fully conserved within the alignment (FIG. 10B). None of the N-terminal domain swaps between NM and ST1 endowed NM with novel properties, suggesting that the ST1 N-terminus is not modular but instead functions in context with other regions of ST1 that were not transferred (FIG. 10C-10F). The C-terminal exchange generated a NM-ST1 hybrid that was capable of interacting with the ST1 crRNA:tracrRNA complex and was further able to suppress a reporter with a ST1 specific PAM (FIG. 10E). This result was further validated with an additional ST1 specific reporter as shown in FIG. 11(A)-11(D).

The invention claimed is:

1. A method of making a mutant Cas9 protein comprising identifying one or more amino acid sequences within a family of Cas9 proteins that are not highly conserved or have low conservation, wherein the one or more amino acid sequences that are not highly conserved or have low conservation are identified by obtaining a sequence alignment of multiple Cas9 amino acid sequences, and by identifying stretches of low conservation or stretches between conservation edges, wherein the conservation of said amino acid sequences is calculated as the relative entropy of amino acid frequencies per position,
identifying a nucleic acid sequence encoding the one or more identified amino acid sequences,
generating a nucleic acid sequence encoding a target Cas9 protein which lacks the nucleic acid sequence encoding the one or more identified amino acid sequences, and
generating a mutant Cas9 protein from the generated nucleic acid sequence, wherein the mutant Cas9 protein retains DNA binding activity.

2. The method of claim 1 wherein the target Cas9 protein has nuclease activity.

3. The method of claim 1 wherein the target Cas9 protein is a nickase.

4. The method of claim 1 wherein the target Cas9 protein is nuclease null.

5. The method of claim 1 wherein the nucleic acid sequence encoding the one or more identified amino acid sequences is deleted from a nucleic acid sequence encoding the target Cas9 protein.

6. The method of claim 1 wherein the nucleic acid sequence encoding the one or more identified amino acid sequences is deleted from a nucleic acid sequence encoding the target Cas9 protein and replaced with a linker.

7. The method of claim 1 wherein the nucleic acid sequence encoding the one or more identified amino acid sequences is deleted from a nucleic acid sequence encoding the target Cas9 protein and replaced with a SGGGS linker.

8. The method of claim 1 wherein the method further comprises
identifying one or more amino acid sequences within a family of Cas9 proteins that are of either high conservation or low conservation wherein each of the high or low conservation sequences is flanked by two flanking amino acid sequences of either low conservation or high conservation, respectively.

9. The method of claim 8 wherein each of the one or more amino acid sequences has a pair of edge amino acid sequences distinguishing the one or more amino acid sequences from flanking amino acid sequences.

10. The method of claim 1 wherein the mutant Cas9 protein is a mutant Cas9 protein encoded by the nucleic acid sequence of SEQ ID NO:1.

11. The method of claim 1 wherein the mutant Cas9 protein is a mutant Cas9 protein encoded by the nucleic acid sequence of SEQ ID NO:2.

* * * * *